(12) United States Patent
Moenning

(10) Patent No.: US 6,783,513 B2
(45) Date of Patent: Aug. 31, 2004

(54) BODY CAVITY ACCESS ASSEMBLY AND AN ASSOCIATED MEDICAL PROCEDURE FOR DISPENSING A LIQUID

(76) Inventor: Stephen P. Moenning, 1940 Jamaica Way, Punta Gorda, FL (US) 33950

( * ) Notice: Subject to any disclaimer, the term of this patent is extended or adjusted under 35 U.S.C. 154(b) by 66 days.

(21) Appl. No.: 10/157,315

(22) Filed: May 29, 2002

(65) Prior Publication Data

US 2002/0193734 A1 Dec. 19, 2002

Related U.S. Application Data

(63) Continuation-in-part of application No. 09/860,048, filed on May 17, 2001, now abandoned.
(60) Provisional application No. 60/294,027, filed on May 29, 2001.

(51) Int. Cl.[7] ...................... A61M 5/178; A61M 25/00; A61M 5/32
(52) U.S. Cl. ................... 604/164.02; 604/265
(58) Field of Search ................. 604/93.01, 96.01, 604/103.01, 103.07, 104, 112, 118, 164.01, 164.03, 167.01, 167.03, 167.05, 246, 247, 248, 263, 272, 523

(56) References Cited

U.S. PATENT DOCUMENTS

| | | |
|---|---|---|
| 3,598,127 A | 8/1971 | Wepsic ...................... 128/349 |
| 3,916,903 A | 11/1975 | Pozzi ...................... 128/305.3 |
| 4,515,593 A | 5/1985 | Norton ....................... 604/265 |
| 4,540,411 A | 9/1985 | Bodicky ...................... 604/169 |
| 4,578,075 A | 3/1986 | Urquhart et al. ............ 604/892 |
| 4,999,210 A | 3/1991 | Solomon et al. ................ 427/2 |
| 5,013,296 A | 5/1991 | Buckberg et al. ............. 604/44 |
| 5,201,714 A | 4/1993 | Gentelia et al. ............ 604/167 |
| 5,250,038 A | 10/1993 | Melker et al. .............. 604/264 |
| 5,344,411 A | 9/1994 | Domb et al. ................ 604/265 |
| 5,385,547 A | 1/1995 | Wong et al. ................... 604/87 |
| 5,397,307 A | 3/1995 | Goodin ........................ 604/96 |
| 5,451,424 A | 9/1995 | Solomon et al. ............. 427/2.1 |
| 5,484,406 A | 1/1996 | Wong et al. ................... 604/87 |
| 5,533,986 A | 7/1996 | Mottola et al. ............. 604/264 |
| 5,567,495 A | 10/1996 | Modak et al. ............. 428/36.9 |
| 5,599,321 A | 2/1997 | Conway et al. ............. 604/265 |
| 5,607,417 A | 3/1997 | Batich et al. ............ 604/890.1 |
| 5,647,859 A | 7/1997 | Lampropoulos et al. ...... 604/53 |
| 5,647,860 A | 7/1997 | Roth et al. .................. 604/264 |
| 5,665,076 A | 9/1997 | Roth et al. ................... 604/53 |
| 5,772,639 A | 6/1998 | Lampropoulos et al. .... 604/264 |
| 5,797,886 A | 8/1998 | Roth et al. .................. 604/153 |
| 5,797,899 A | 8/1998 | Tilton, Jr. ...................... 606/1 |
| 5,800,378 A | 9/1998 | Edwards et al. .............. 604/21 |
| 5,817,072 A | 10/1998 | Lampropoulos et al. .... 604/264 |
| 5,817,073 A | 10/1998 | Krespi ........................ 604/272 |
| 5,830,192 A | 11/1998 | Van Voorhis ............... 604/280 |
| 5,843,017 A | 12/1998 | Yoon ........................... 604/22 |
| 5,895,370 A | 4/1999 | Edwards et al. .............. 604/22 |
| 5,968,008 A | 10/1999 | Grams ......................... 604/35 |
| 5,972,013 A | 10/1999 | Schmidt ..................... 606/185 |
| 5,984,942 A | 11/1999 | Alden et al. ................ 606/190 |
| 5,997,497 A | 12/1999 | Nita et al. .................... 604/22 |
| 6,004,302 A | 12/1999 | Brierley ...................... 604/264 |
| 6,056,766 A | 5/2000 | Thompson et al. ......... 606/185 |

Primary Examiner—Brian L. Casler
Assistant Examiner—Mark K Han
(74) Attorney, Agent, or Firm—Wood, Herron & Evans, L.L.P.

(57) ABSTRACT

A body cavity access assembly includes a conduit having an exterior surface, a dispensing mechanism, and a reservoir for receiving a biologically active compound. The exterior surface of the conduit has first exit port and a second exit port defined therein which are in fluid communication with the reservoir. The first exit port and the second exit port are selectively positionable between an open mode of operation and a closed mode of operation with the dispensing mechanism. An associated medical procedure for dispensing a biologically active compound is also disclosed.

17 Claims, 16 Drawing Sheets

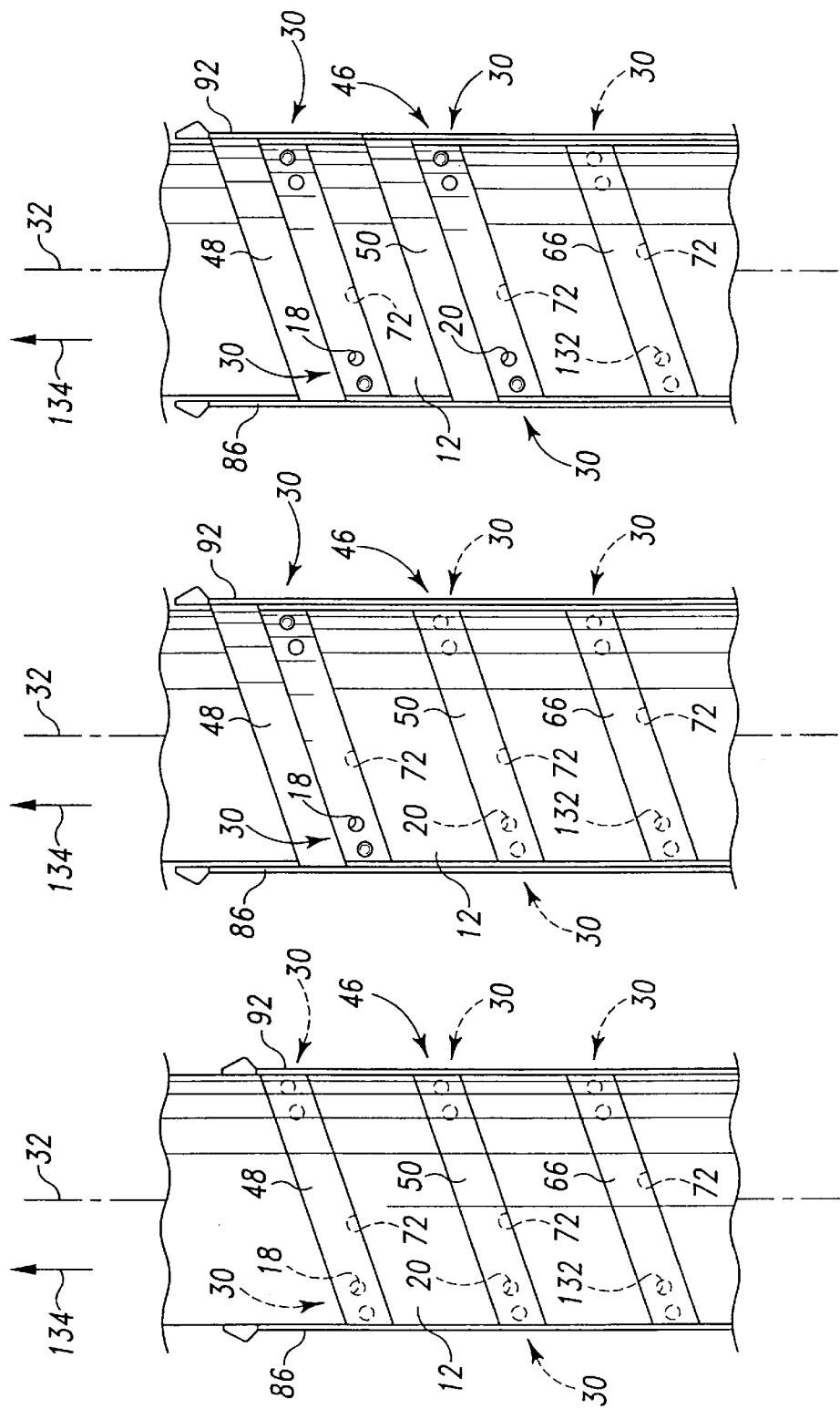

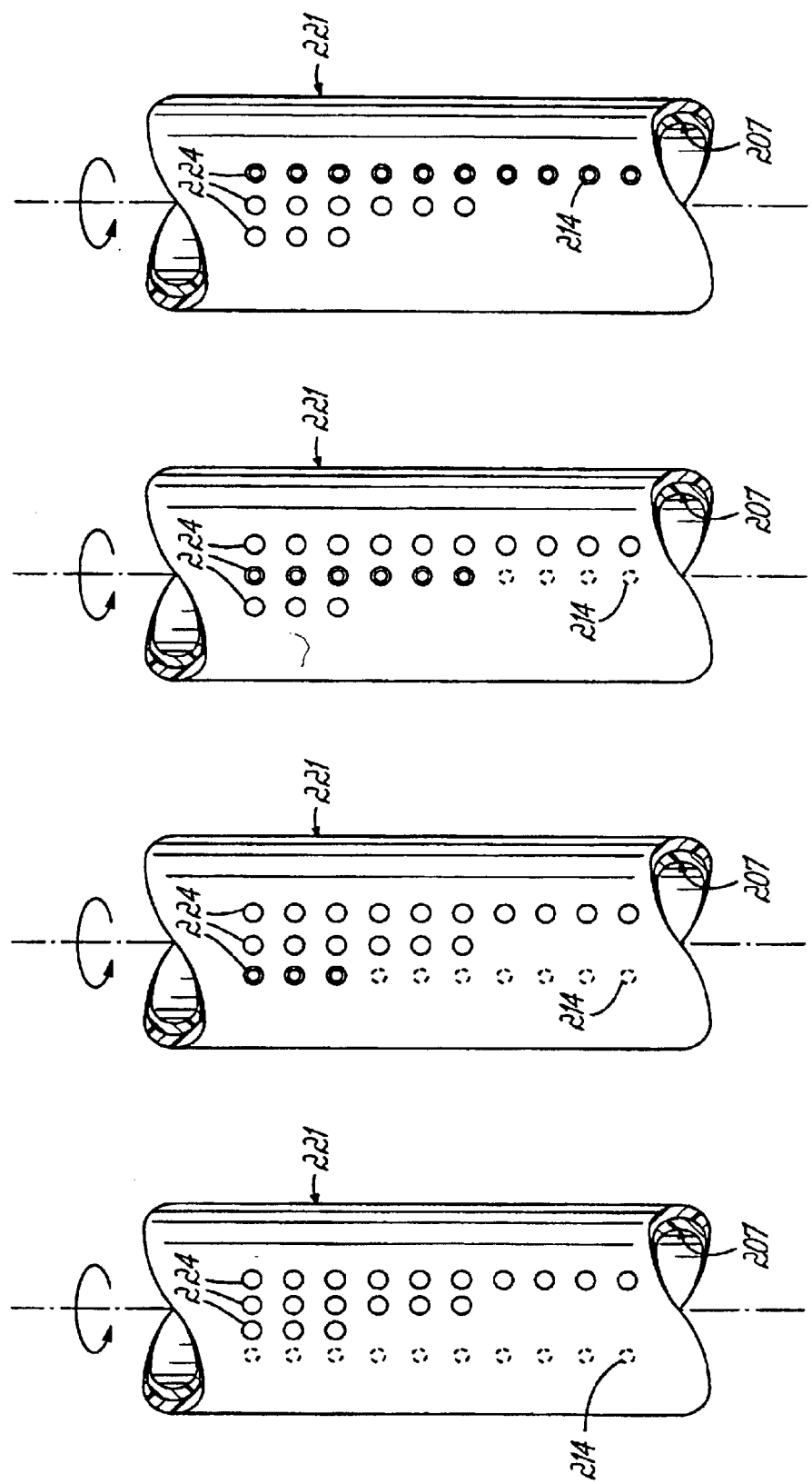

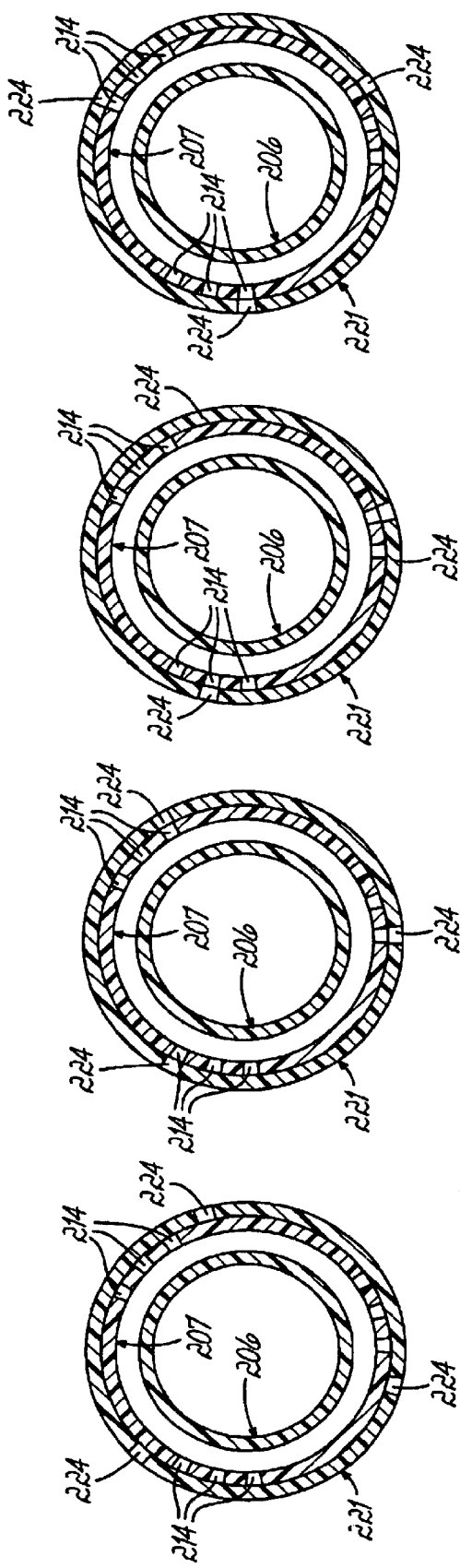

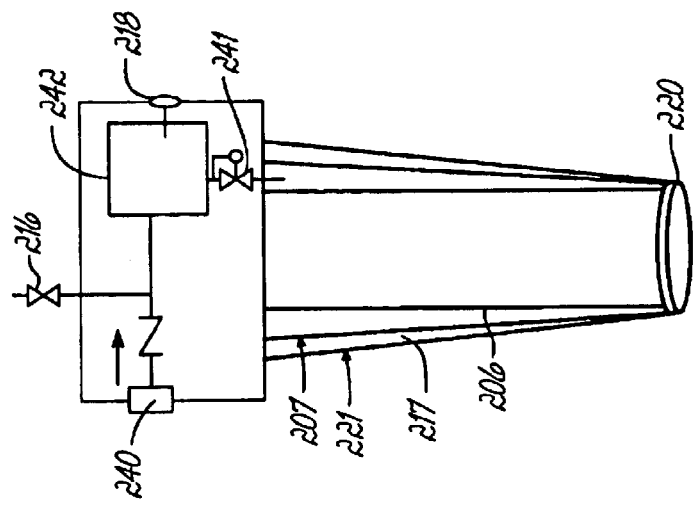
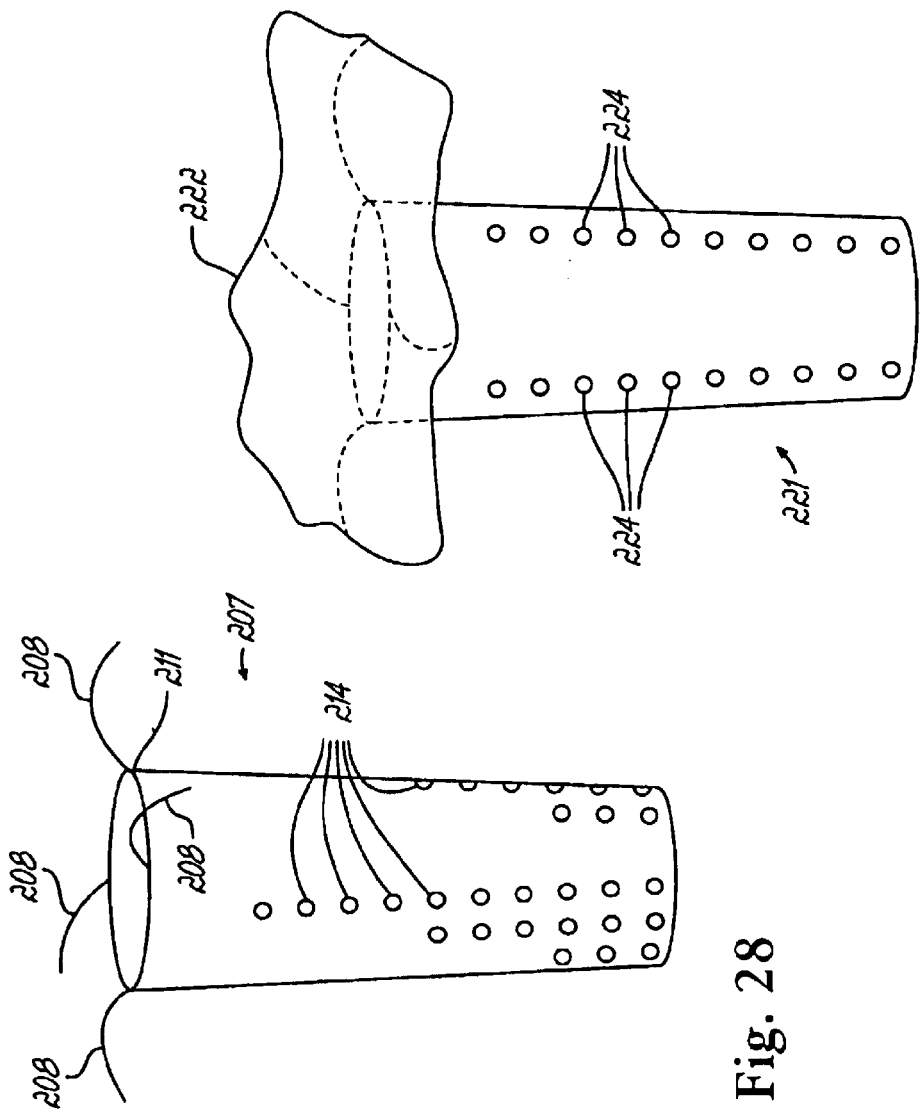
Fig. 30
Fig. 29
Fig. 28

BODY CAVITY ACCESS ASSEMBLY AND AN ASSOCIATED MEDICAL PROCEDURE FOR DISPENSING A LIQUID

The present application is a continuation-in-part of application Ser. No. 09/860,048 filed on May 17, 2001, now abandoned, and also claims the benefit of provisional patent application Serial No. 60/294,027, filed May 29, 2001 (now pending). The disclosures of each of these prior related applications are hereby fully incorporated by reference herein.

BACKGROUND OF THE INVENTION

The present invention relates to a body cavity access assembly and a procedure for dispensing a liquid, which may contain a biologically active compound, into a patient.

Minimally invasive surgical techniques, such as laparoscopic surgery, typically include the use of a trocar assembly. A trocar assembly includes an obturator (also known as a trocar) positioned within the channel of a cannula. The obturator and cannula are advanced through a body cavity wall so as to create a small opening or a port site wound therein. The obturator is then completely removed from the lumen of the cannula such that the cannula's channel provides an entrance for laparoscopic instruments into the interior of the body cavity. The body cavity is then insufflated with an inert gas, such as CO2, to provide easier access and visualization of the organs contained therein. An alternative to insufflation, which also aids in intra-abdominal visualization and provides access to the organs, is a mechanical lifting device. Once the surgery is complete the cannula is completely removed from the port site wound to rapidly desufflate the body cavity.

Surgery performed in this manner is associated with a lower post-operative pain, quicker recovery and improved immune function. (1, 2, 3, 4, 5, 6). Because of these advantages, laparoscopic surgery has experienced exponential growth. Benign laparoscopic surgery is now well accepted, and surgeons have progressed into the next field of laparoscopic surgery, i.e. laparoscopic cancer surgery. In particular, laparoscopic colon cancer surgery is now being evaluated in a National Institute of Health study. An initial result from this study confirms the laparoscopic method does have advantages over the conventional open surgery. (5, 6, 14).

However, the development of laparoscopic surgery for cancer has been hindered because of the major concern regarding the implantation of tumor cells in the port site wound. (2, 3, 6, 7). In fact, numerous port site recurrences have been documented in the medical literature heretofore, and these recurrences are associated with a decreased survival rate for patients who may have had a curative cancer (2, 3, 6, 7).

Specifically, the medical literature reports that the incidence of tumor cell implantation ranges from as high as 20% to a low of 0% (8). The follow-up evaluation of this wide incidence of port site implantation places a large emphasis on the surgeons learning curve. In particular, the beginning surgeon (less than 25–50 cases) will have a much higher incidence of port site implantation than the advanced surgeon (greater than 50 cases). In spite of using some of the most advanced surgeons in the world, the NIH study confirms an incidence of 1.3% port site implantation for laparoscopic methods (10) as compared to a 0.6% incidence for the open techniques (9).

Several mechanisms may be responsible for the above discussed implantation of tumor cells in the port site wound. For example, minimally invasive surgical techniques for treating cancer require the insertion and removal of laparoscopic instruments or cameras through the lumen of the cannula. In addition, these surgical techniques require that the cannula itself be moved relative to the port site wound such that the cannula is advanced further into, or withdrawn from, the body cavity (11). Moving the cannula in the above-described manner facilitates a surgeon's ability to optimally locate instruments within the body cavity thereby helping to ensure the successful completion of the medical procedure. However, the aforementioned manipulations of the laparoscopic instruments and cannula may result in the exposure of the port site wound to exfoliated cancer cells which creates a risk of implanting tumor cells in the walls of the port site wound (11, 12). In particular, exfoliated cancer cells may adhere to and thus contaminate a portion of the exterior surface of the cannula (11, 12). The contaminated portion of the exterior surface of the cannula may then be advanced into contact with the port site wound during insertion and removal from the port site wound (11, 12). This contact may dislodge the exfoliated cancer cells from the exterior surface of the cannula and thus cause the exfoliated cancer cells to be implanted in the port site wound (11, 12).

As briefly mentioned above, studies have shown that a physician will undergo a significant learning curve before becoming proficient in the performance of advanced laparoscopic surgery, such as cancer surgery (3, 13, 16). As a result, a relatively inexperienced surgeon may have a tendency to manipulate or handle a tumor to a greater degree during a surgical procedure than an experienced surgeon. For example, studies have shown a 14.6% incidence of viable tumor cells in proximity of the specimen where the surgeon is working with his or her instruments (15). In addition, an inexperienced surgeon may have a tendency to insert and withdraw an instrument through the lumen of the cannula a greater number of times than an experienced surgeon. The above-described increased manipulation of the instrument or the tumor can result in a greater incidence of tumor cell implantation in the port site wound.

Regardless of how these cells contaminate the wound, once implanted therein, viable tumor cells can cause a subcutaneous metastases or "port site recurrence" after the resection of malignant tissue. These "port site recurrences" have delayed the advancement of laparoscopic cancer surgery (2, 6, 7, 8, 9, 10, 11, 12) into all fields of cancer surgery, and is one reason why the benefits of laparoscopic surgery have not been available to cancer patients.

Furthermore, laparoscopic surgery performed for general surgery, gynecological surgery, urological surgery, or any other intraabdominal/intra-thoracic infection is associated with a small but real incidence of port site wound infection (1). The infecting bacteria causing these illnesses can contaminate the port site wound in the same manner as discussed above with regard to tumor cell contamination, and these infections can increase a patient's morbidity and consequently the length of a patient's hospital stay, thereby increasing their hospital bill.

What is needed therefore is an assembly and procedure which addresses on or more of the above described drawbacks and may be used for other situations in which dispensing a liquid during a laparoscopic or similar procedure would be desirable.

TABLE OF REFERENCES CITED IN THE BACKGROUND

1. Lord et al., *Dis. Col. Rect.* 39(2):148 (1996)
2. Berman, *Important Advances in Oncology* 1996, *Laparoscopic Resection for Colon Cancer: Cause for Pause*, Vincent DeVita Ed., p. 231
3. Falk et al., *Dis. Col. Rect.* 36:28 (1993)
4. Liberman et al., *Surg. Endo.* 10:15 (1996)
5. Whelan et al., *Dis. Col. Rect.* 41(5):564 (1998)
6. Wexner et al., *Am. Surg.* 64(1):12–18 (1998)
7. Greene, *Semin. Lap. Surg.* 2(3):153 (1995)
8. Kazemier, *Surg. Endo.* 9:216 (1995)
9. Reilly et al., *Dis. Col. Rect.* 39(2):200 (1996)
10. Jacquet et al., *Dis. Col. Rect.* 38(10):140 (1995)
11. Reymond et al., *Surg. Endo.* 11:902 (1997)
12. Allardyce et al., *Dis. Col. Rect.* 40(8):939 (1997)
13. Caushaj et al., *Dis. Col. Rect.* 37(4):21 (Podium Abstract 1994)
14. Lee et al., (*oral presentation, 6$^{th}$ World Congress of Endoscopic Surgery*, June 1998) *Surgical Endoscopy* 12 (5):14 (1998)
15. Russell et al., *Dis. Col. Rect.* 40(11):1294 (1997)
16. Neuhaus S J, (*oral presentation, 6$^{th}$ World Congress of Endoscopic Surgery*, June 1998) *Surgical Endoscopy* 12 (5): 515 (1998)
17. Schneider C, (*oral presentation, 6$^{th}$ World Congress of Endoscopic Surgery*, June 1998) *Surgical Endoscopy* 12 (5): 517 (1998)

SUMMARY OF THE INVENTION

The invention generally relates to a body cavity access assembly including a conduit having a lumen through which a medical instrument may be advanced, an exterior surface, a liquid input adapted to be coupled to a source of liquid, and communicating with a plurality of exit ports defined along a portion of the exterior surface. A dispensing mechanism is operatively coupled to the conduit and is adjustable to selectively open the exit ports to allow the liquid to flow therefrom and also to selectively close at least one of the exit ports to prevent the liquid from flowing.

The invention also generally relates to a method for dispensing a liquid during a surgical procedure. The method includes creating an opening in a wall of a body cavity and advancing a conduit through the opening. The conduit includes a lumen through which a medical instrument may be advanced and further includes an exterior surface having a variable sized dispensing zone extending along a length thereof. The method further includes discharging the liquid from the dispensing zone, changing the size of the dispensing zone, and discharging the liquid from the dispensing zone of changed size.

In accordance with one more specific embodiment of the present invention, there is provided a body cavity access assembly. The assembly includes a conduit having (i) a lumen through which a medical instrument may be advanced, (ii) an exterior surface, (iii) a first exit port defined in the exterior surface, and (iv) a second exit port defined in the exterior surface. The assembly also includes a reservoir having an interior void for receiving a biologically active compound. The interior void of the reservoir is in fluid communication with the first exit port and the second exit port. The assembly further includes a dispensing mechanism operatively coupled to the conduit. The dispensing mechanism is positionable between a first position, a second position, and a third position. When the dispensing mechanism is positioned in the first position the biologically active compound is prevented from being advanced through the first exit port and the second exit port. When the dispensing mechanism is positioned in the second position the biologically active compound is advanced through the first exit port, and prevented from being advanced through the second exit port. When the dispensing mechanism is positioned in the third position the biologically active compound is advanced through the first exit port and the second exit port.

Pursuant to another embodiment of the present invention, there is provided a body cavity access assembly. The assembly includes a reservoir having an interior void for receiving a biologically active compound. The assembly also includes a conduit having (i) a lumen through which a medical instrument may be advanced, (ii) an exterior surface, (iii) a first exit port defined in the exterior surface, the first exit port being (A) operable between an open mode of operation and a closed mode of operation and (B) in fluid communication with the interior void of the reservoir and (iv) a second exit port defined in the exterior surface, the second exit port being (A) operable between an open mode of operation and a closed mode of operation and (B) in fluid communication with the interior void of the reservoir. The assembly further includes a dispensing mechanism operatively coupled to the first exit port and the second exit port, such that (i) the dispensing mechanism can selectively place the first exit port in (A) the open mode of operation so that the biologically active compound is advanced through the first exit port or (B) the closed mode of operation so that the biologically active compound is prevented from being advanced through the first exit port and (ii) the dispensing mechanism can selectively place the second exit port in (A) the open mode of operation so that the biologically active compound is advanced through the second exit port or (B) the closed mode of operation so that the biologically active compound is prevented from being advanced through the first exit port.

According to yet another embodiment of the present invention, there is provided a medical procedure for dispensing a biologically active compound. The method includes creating an opening in a wall of a body cavity. The method also includes advancing a body access assembly through the opening and into the body cavity. The body access assembly includes (1) a reservoir having an interior void for receiving a biologically active compound, (2) a conduit having (i) a lumen through which a medical instrument may be advanced, (ii) an exterior surface, (iii) a first exit port defined in the exterior surface, the first exit port being (A) operable between an open mode of operation and a closed mode of operation and (B) in fluid communication with the interior void of the reservoir and (iv) a second exit port defined in the exterior surface, the second exit port being (A) operable between an open mode of operation and a closed mode of operation and (B) in fluid communication with the interior void of the reservoir; and (3) a dispensing mechanism operatively coupled to the first exit port and the second exit port, such that (i) the dispensing mechanism can selectively place the first exit port in (A) the open mode of operation so that the biologically active compound is advanced through the first exit port or (B) the closed mode of operation so that the biologically active compound is prevented from being advanced through the first exit port and (ii) the dispensing mechanism can selectively place the second exit port in (A) the open mode of operation so that the biologically active compound is advanced through the second exit port or (B) the closed mode of operation so that the biologically active compound is prevented from being advanced through the first exit port. The method also includes selectively placing the first exit port in the open mode of operation with the dispensing mechanism. The method further includes advancing the biologically active compound from the interior void of the reservoir through the first exit port.

In accordance with another embodiment of the present invention, there is provided a body cavity access assembly. The assembly includes a conduit having (i) a lumen through which a medical instrument may be advanced, (ii) an exterior surface, and (iii) an exit port defined in the exterior surface. The assembly also includes a reservoir having an interior void for receiving a biologically active compound. The interior void of the reservoir is in fluid contact with the exit port. The assembly further includes a dispensing mechanism operatively coupled to the conduit. The dispensing mechanism is positionable between a first position and a second position. When the dispensing mechanism is positioned in the first position the biologically active compound is prevented from being advanced through the exit port. When the dispensing mechanism is positioned in the second position, the biologically active compound is advanced through the exit port.

Pursuant to another embodiment of the present invention, there is provided a body cavity access assembly. The assembly includes a reservoir having an interior void for receiving a biologically active compound. The assembly also includes a conduit having (i) a lumen through which a medical instrument may be advanced, (ii) an inside sleeve, (iii) a first exit port defined in the inside sleeve, the first exit port being operable between an open mode of operation and a closed mode of operation and in fluid communication with the interior void of the reservoir, (iv) a second exit port defined in the inside sleeve, the second exit port being operable between an open mode of operation and a closed mode of operation and in fluid communication with the interior void of the reservoir, (v) a third exit port defined in the inside sleeve, the third exit port being operable between an open mode of operation and a closed mode of operation and in fluid communication with the interior void of the reservoir. The assembly further includes a dispensing mechanism, an outside sleeve, and alignment ports defined in the outside sleeve. The dispensing mechanism rotates the outside sleeve relative to the inside sleeve and is positionable between a first position, second position, third position and fourth position. When the dispensing mechanism is positioned in the first position the biologically active compound is prevented from being advanced through the exit ports. When the dispensing mechanism is positioned in the second position, the biologically active compound is advanced through the first exit port. When the dispensing mechanism is positioned in the third position, the biologically active compound is advanced through the second exit port. When the dispensing mechanism is positioned in the fourth position, the biologically active compound is advanced through the third exit port. The biologically active compound is delivered to the reservoir from the storage reservoir by the pressure inside the storage reservoir created by the pump. Once the storage reservoir pressure exceeds a limit a relief valve lifts allowing the compound to transfer from the storage reservoir to the reservoir.

Various additional objectives, advantages and features of the invention will become more readily apparent to those of ordinary skill in the art upon review of the detailed description of the illustrative embodiments.

BRIEF DESCRIPTION OF THE DRAWINGS

FIG. 1 is an exploded view of an exemplary body cavity access assembly of the present invention showing a conduit, a base plate, a cannula, and an obturator thereof;

FIG. 2 is an exploded view of an exemplary dispensing mechanism of a body cavity access assembly of the present invention showing a helical member, a number of actuating rods, and a locking ring thereof;

FIG. 3 is an assembled view of a body cavity access assembly of the present invention just prior to being advanced through a body cavity wall;

FIG. 4 is an enlarged fragmentary view of the conduit and the helical member of the body cavity access assembly of FIG. 1, showing the exit ports defined on the conduit in the closed mode of operation;

FIG. 5 is a view similar to FIG. 4, but showing a number of the exit ports defined on the conduit in the open mode of operation while other exit ports defined on the conduit remain in the closed mode of operation;

FIG. 6 is a view similar to FIG. 5, but showing an additional number of the exit ports defined on the conduit in the open mode of operation;

FIG. 7 is a side fragmentary view of a body cavity access assembly of the present invention positioned within an opening created in a body cavity wall;

FIG. 8 is a view similar to FIG. 7 but showing a body cavity access assembly of the present invention positioned within an opening created in a relatively thicker body cavity wall;

FIG. 9 is an enlarged fragmentary view of a helical member of an exemplary dispensing mechanism;

FIG. 10 is an enlarged fragmentary cross sectional view of the body access assembly in FIG. 3 showing a first exit port and a second exit port in a closed mode of operation;

FIG. 11 is a view similar to FIG. 10, but showing the first exit port in an open mode of operation and the second exit port in a closed mode of operation;

FIG. 12 is a side view of the hole orientation of an inside sleeve and an outside sleeve for applying chemical to the distal portion of a port site opening during the filling of the reservoir;

FIG. 12A is a side view of the hole orientation of the inside sleeve and outside sleeve for applying chemical to the proximal portion of a port site opening during the filling of the reservoir;

FIG. 13 is a side view of the hole orientation of the inside sleeve and outside sleeve for applying chemical to the distal portion of a shallow port site opening;

FIG. 13A is a side view of the hole orientation of the inside sleeve and outside sleeve for applying chemical to the proximate portion of a shallow port site opening;

FIG. 14 is a side view of the hole orientation of the inside sleeve and outside sleeve for applying chemical to the distal portion of a medium depth port site opening;

FIG. 14A is a side view of the hole orientation of the inside sleeve and outside sleeve for applying chemical to the proximate portion of a medium depth port site opening;

FIG. 15 is a side view of the hole orientation of the inside sleeve and outside sleeve for applying chemical to the distal portion of a deep port side opening;

FIG. 15A is a side view of the hole orientation of the inside sleeve and outside sleeve for applying chemical to the proximal portion of a deep port side opening;

FIG. 16 is a cross sectional view of FIG. 12 and FIG. 12A where no holes of the inside sleeve align with the holes of the outside sleeve during the filling of the reservoir;

FIG. 17 is a cross sectional view of FIG. 13 and FIG. 13A where the short row of holes of the outside sleeve align with the row of holes of the inside sleeve for applying chemical to a shallow port site opening;

FIG. 18 is a cross sectional view of FIG. 14 and FIG. 14A where the medium length row of holes of the outside sleeve align with the row of holes of the inside sleeve for applying chemical to a medium depth port site opening;

FIG. 19 is a cross sectional view of FIG. 15 and FIG. 15A where the long length row of holes of the outside sleeve align with the row of holes of the inside sleeve for applying chemical to a deep port site opening.

FIG. 28 is a side view of the inside sleeve of one embodiment of the present invention;

FIG. 29 is a side view of the outside sleeve of the embodiment of the present invention represented in FIG. 28; and FIG. 30 is a side view of the assembly of the embodiment of the present invention represented in FIGS. 28 and 29.

DETAILED DESCRIPTION OF THE PREFERRED EMBODIMENTS

Figure 1:
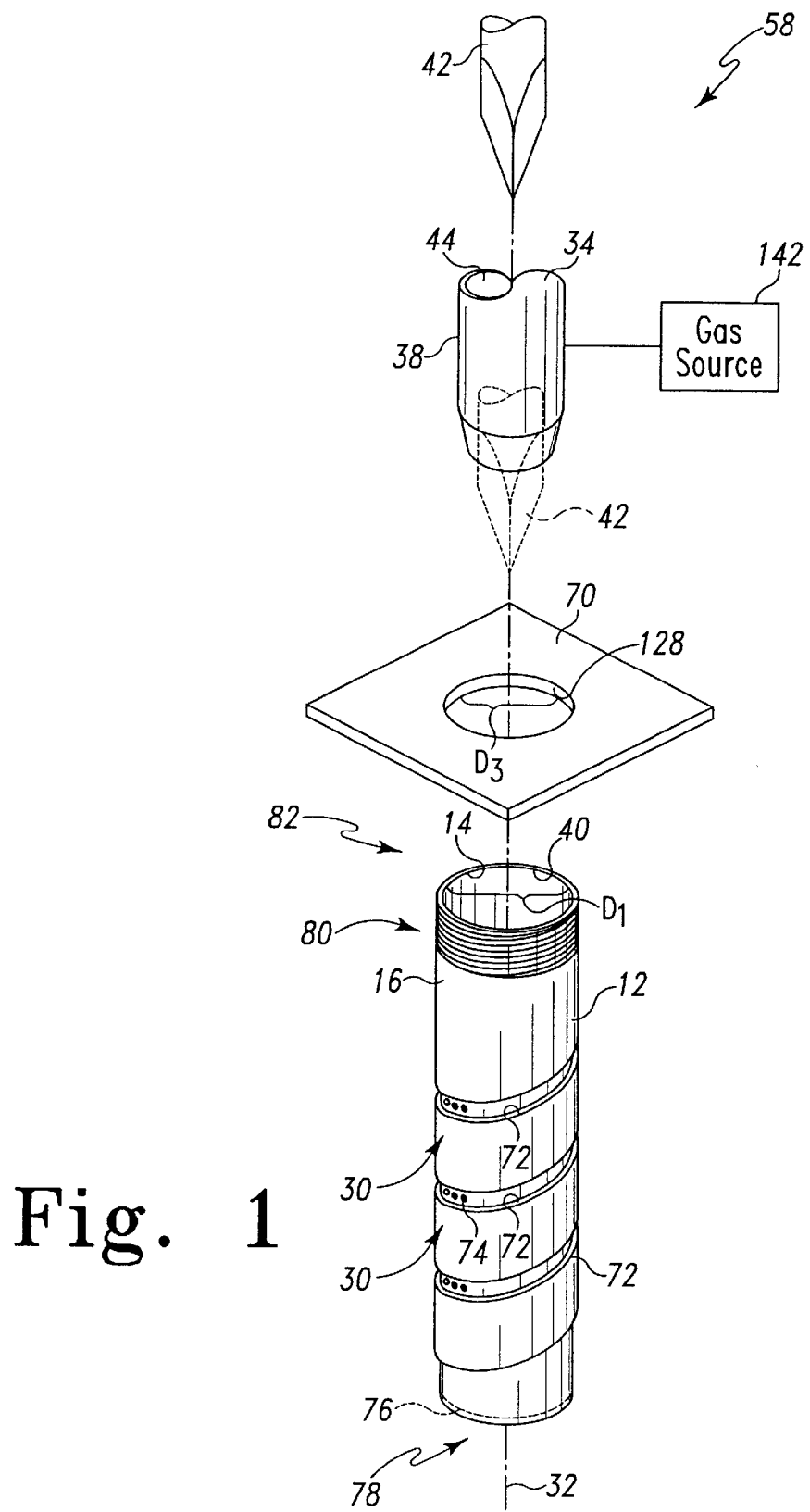

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

THE EMBODIMENTS OF FIGS. 1–11

Figure 2:
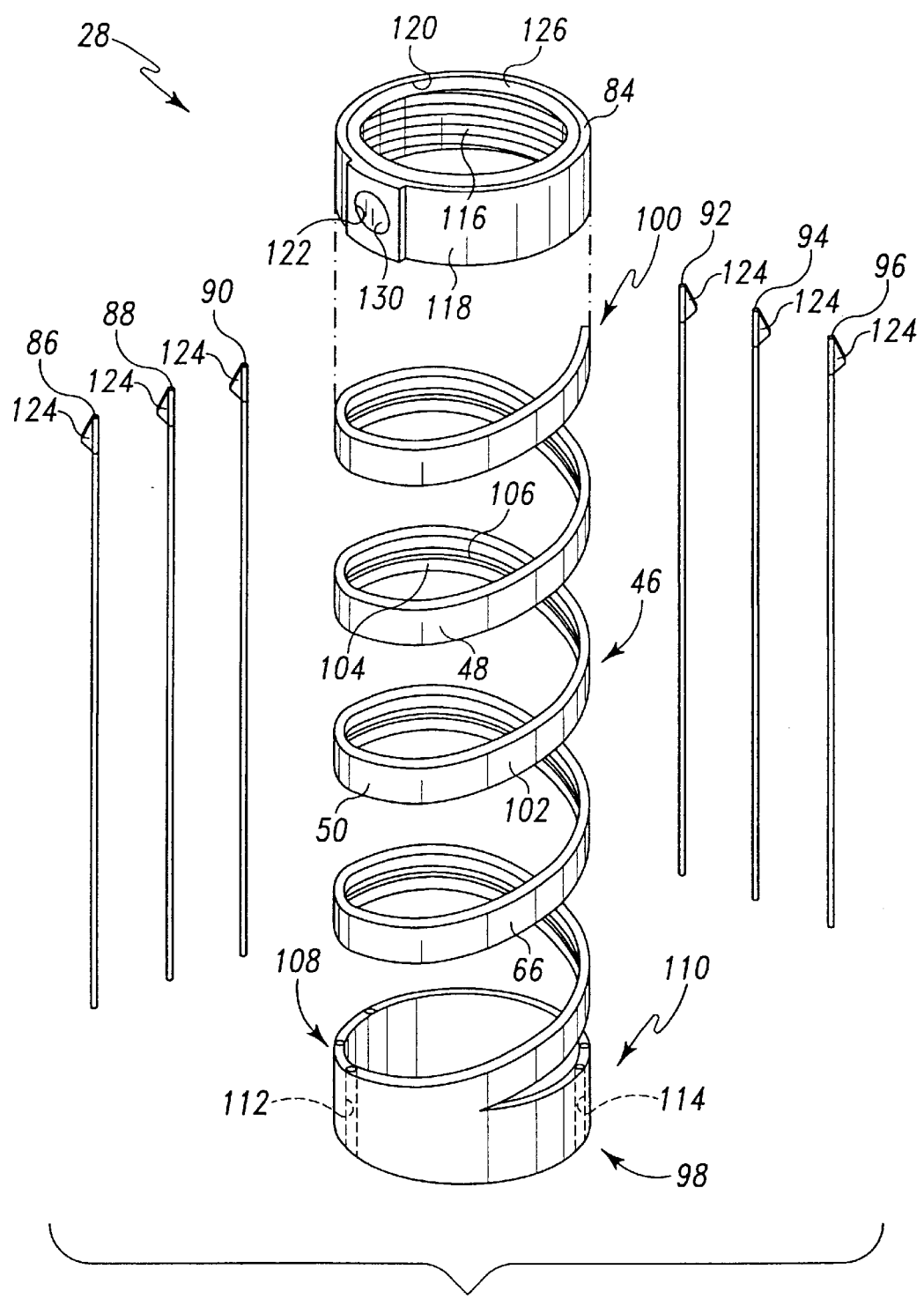
Figure 3:
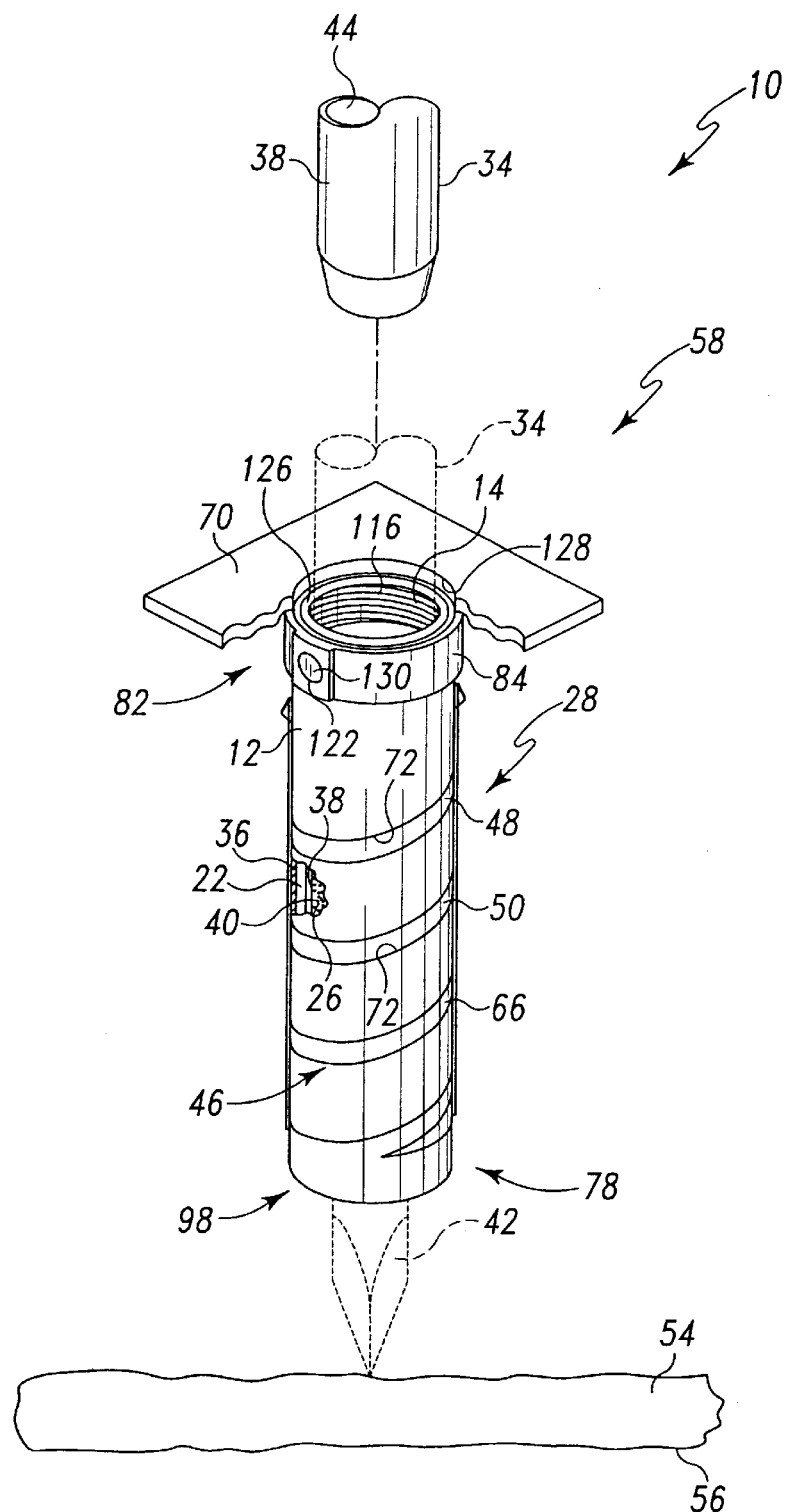

Referring to FIGS. 1, 2, and 3, there is shown an exemplary body cavity access assembly 10 of the present invention. Body cavity access assembly 10 includes a conduit 12, a dispensing mechanism 28, a base plate 70, and a trocar assembly 58. As shown in FIG. 1, conduit 12 has an exterior surface 16 and an interior surface 40. Interior surface 40 defines a lumen 14 which extends through conduit 12. It should be understood that conduit 12 can have a tapered shape so that, for example, a proximal end 82 of conduit 12 can have an inner diameter $D_1$, of about 2 cm which gradually decreases along a longitudinal axis 32 of conduit 12 until a distal end 78 of conduit 12 has an inner diameter $D_2$ of about 1 cm. It should also be understood that, preferably, inner diameter $D_2$ of conduit 12 is greater than, or equal to, 5 mm so as to allow medical instruments, such as a laparoscopic camera, to be advanced through lumen 14 of conduit 12.

Still referring to FIG. 1, exterior surface 16 of conduit 12 has helical groove 72 defined therein which extends along longitudinal axis 32. In addition, exterior surface 16 of conduit 12 has a plurality of exit ports 30 defined therein so that exterior surface 16 is in fluid communication with lumen 14. Exit ports 30 are positioned on exterior surface 16 so that exit ports 30 are located within helical groove 72 and extend along longitudinal axis 32. Exterior surface 16 of conduit 12 also has a number of guides 74 extending therefrom. Guides 74 are positioned on exterior surface 16 so that guides 74 are located within helical groove 72 and are adjacent to exit ports 30. A bearing member 76, for example a rubber O-ring, is secured (e.g. with an adhesive) to interior surface 40 of conduit 12 near distal end 78 of conduit 12. In addition, a number of threads 80 are defined on exterior surface 16 near proximal end 82 of conduit 12.

Figure 9:
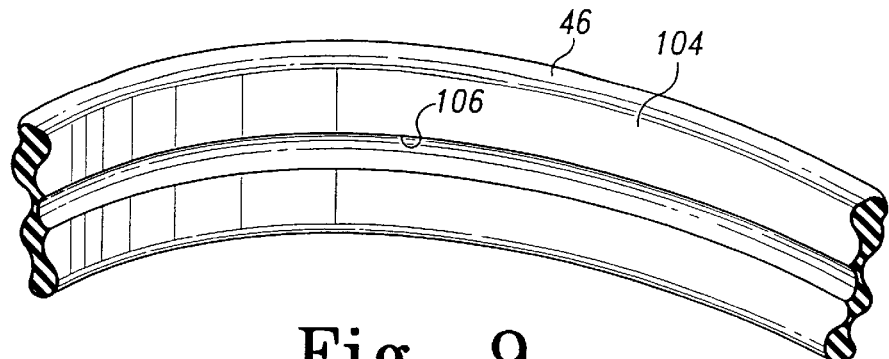

Referring now to FIG. 2, an exemplary dispensing mechanism includes a helical member 46, a locking ring 84, and actuation rods 86, 88, 90, 92, 94, and 96. Each actuation rod 86, 88, 90, 92, 94, and 96 has a tab 124 attached to an end thereof. Helical member 46 has an end portion 98, an end portion 100, a helical portion 48, a helical portion 50 and a helical portion 66. Helical member 46 also has an exterior surface 102 and an interior surface 104. As shown more clearly in FIG. 9, a helical groove 106 is defined on interior surface 104 of helical member 46. A left side 108 of end portion 98 has three slots defined therein. However, only one slot, i.e. slot 112, is completely shown in FIG. 2 but it should be understood that the other two slots are (i) substantially identical to slot 112 and (ii) positioned adjacent to slot 112. In a similar manner, a right side 110 of end portion 98 also has three slots defined therein. However, once again, only one slot, i.e. slot 114, is completely shown in FIG. 2 but it should be understood that the other two slots are (i) substantially identical to slot 114 and (ii) positioned adjacent to slot 114. End portion 100 of helical member 46 is secured to locking ring 84 for example with an adhesive.

Still referring to FIG. 2, locking ring 84 has an interior surface 116 and an exterior surface 118. Threads 120 are defined on interior surface 116 of locking ring 84. Exterior surface 118 has an injection port 122 defined therein. Injection port 122 extends all the way through locking ring 84 so that exterior surface 118 and interior surface 116 are in fluid communication. If desired, a rubber diaphragm 130 can be positioned within injection port 122. A bearing member 126, e.g. an O-ring, is attached to interior surface 116 (e.g. with an adhesive) of locking ring 84.

Now referring back to FIG. 1, base plate 70 has a hole 128 defined therethrough. Hole 128 has a diameter $D_3$. Preferably, diameter $D_3$ is substantially the same as inner diameter $D_1$ of proximal end 82 of conduit 12.

Still referring to FIG. 1, trocar assembly 58 includes a cannula 34 and an obturator 42. Cannula 34 has a passageway 44 extending therethrough. Obturator 42 is positionable within passageway 44, or is completely removable from obturator 42. In addition, passageway 44 is operatively coupled to a gas source 142, such as $CO_2$, in a well known manner such that a gas can be advanced through passageway 44.

As shown in FIG. 3, helical member 46 is disposed around conduit 12 such that helical member 46 is positioned within helical groove 72 and covers the plurality of exit ports 30. Furthermore, helical member 46 is positioned within helical groove 72 so that a portion of each guide 74 (see FIGS. 1, 10, and 11) extends into helical groove 106 defined on interior surface 104 of helical member. In addition, end portion 98 of helical member 46 is attached (e.g. by an adhesive) to distal end 78 of conduit 12. Locking ring 84 is disposed around proximal end 82 of conduit 12 so that threads 120 defined on interior surface 116 (see FIG. 2) of locking ring 84 meshingly engage with threads 80 (see FIG. 1) defined on exterior surface 16 of conduit 12. Locking ring 84 is also positioned relative to conduit 12 so that injection port 122 is located above proximal end 82 of conduit 12.

Each actuating rod 86, 88, 90, 92, 94, and 96 is positioned relative to helical member 46 so that and end thereof is slidably disposed within a slot defined in end portion 98. For example, as shown in FIG. 2, an end of actuating rod 86 opposite to the end having tab 124 attached thereto is slidably disposed within slot 112, while an end of actuating rod 92 opposite to the end having tab 124 attached thereto is slidably disposed within slot 114. The ends of actuating rods 88 and 90 are also slidably disposed into the two other slots defined in left side 108 of end portion 98 in a substantially identical manner as that described for actuating rod 86. Likewise the ends of actuating rods 94 and 96 are slidably disposed into the two other slots defined in right side 110 of end portion 98 in a substantially identical manner as that described for actuating rod 92. Positioning each actuating rod 86, 88, 90, 92, 94, and 96 in the above described manner results in each actuating rod 86, 88, 90, 92, 94, and 96 being in a substantially parallel relationship with longitudinal axis 32 of conduit 12. It should be understood that once positioned in the above described manner, helical portion 48 is secured (e.g. with an adhesive) to actuating rods 86 and 92, helical portion 50 is secured to actuating rods 88 and 94, and helical portion 66 is secured to actuating rods 90 and 96.

It should be appreciated that attaching the actuating rods of dispensing mechanism 28 to the specific helical portions as described above results in the ability to selectively move one helical portion relative to conduit 12 independently of the other two helical portions. For example, as shown in FIGS. 4 and 5, moving actuating rods 86 and 92 along longitudinal axis 32 of conduit in the direction indicated by arrow 134 results in helical portion 48 also being moved relative to conduit 12 while helical portions 50 and 66 remain stationary. Thus it should be understood that helical member 46 is constructed from a material which is pliable enough so that helical portions 48, 50, and 66 can be moved relative to one another and relative to conduit 12. For example, one material helical member 46 can be made from is silicone rubber. Moreover, it should be appreciated that moving actuating rods 86 and 92, and helical portion 48, in the above described manner results in helical portion 48 being moved out of helical groove 72 and away from the exit ports positioned therein as shown in FIG. 5. However, note that the actuating rod is only moved a distance sufficient to move the helical portion (e.g. helical portion 48) away from the desired exit ports while end of the actuating rod remains positioned in the corresponding slot (e.g. slot 112 for actuating rod 86) defined in end portion 98 of helical member 46. In addition, moving the actuating rods 86, and helical portion 48, in the above described manner results in the guide 74 positioned adjacent to helical portion 48 being removed from helical groove 106 (see FIG. 9). It should be understood that moving helical portion 48 away from the exit ports positioned thereunder allows a fluid to be advanced through such exit ports, for example, exit port 18 shown in FIG. 5. On the other hand, having helical portion 48 positioned over the exit ports, prevents a fluid from being advanced through the exit ports. In other words, coupling actuating rods 86, 88, 90, 92, 94, and 96 and helical member 46 of dispensing mechanism 28 to conduit 12 and the plurality of exit ports 30 in the above described manner allows one to selectively place a specific exit port defined in conduit 12 in (i) an open mode of operation (i.e. the helical portion is moved away from the exit port) so that a fluid can be advanced through the selected exit port or (ii) a closed mode of operation (i.e. the helical portion is disposed over the exit port) so that fluid is prevented from being advanced through the exit port.

Figures 10, 11:
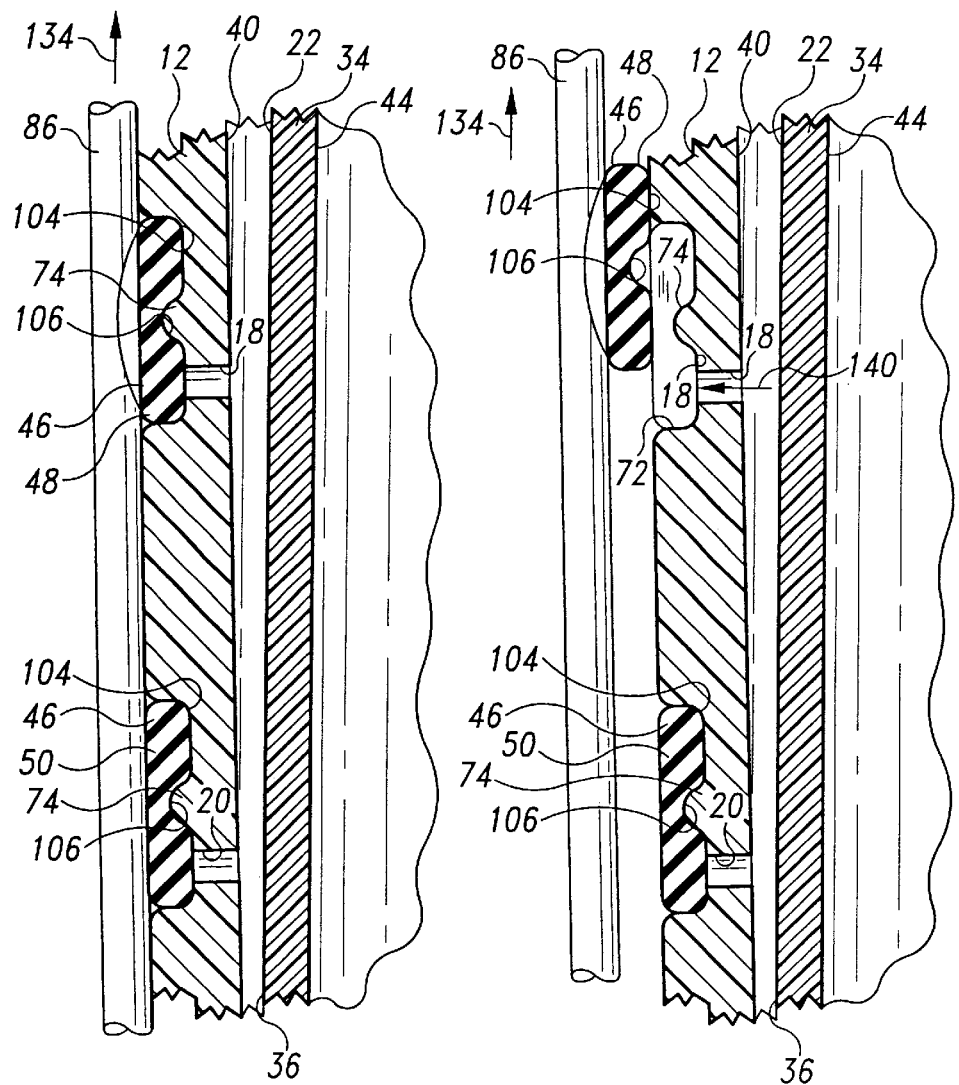
Figure 15A:
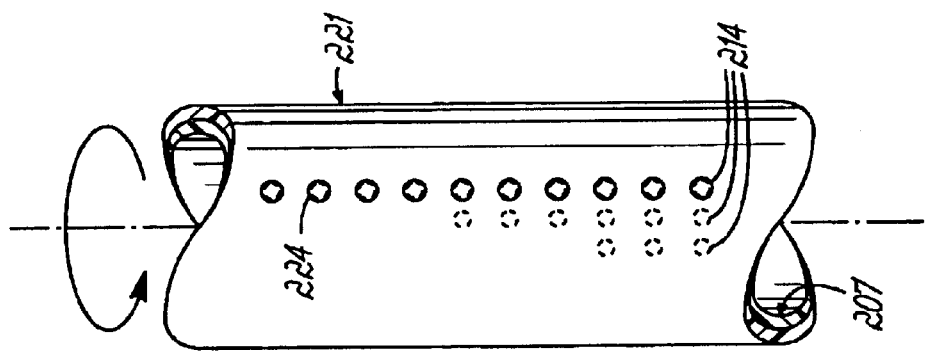
Figure 14A:
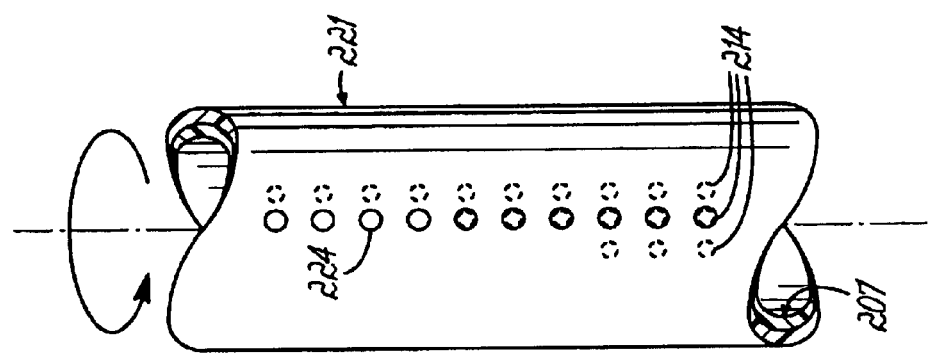
Figure 13A:
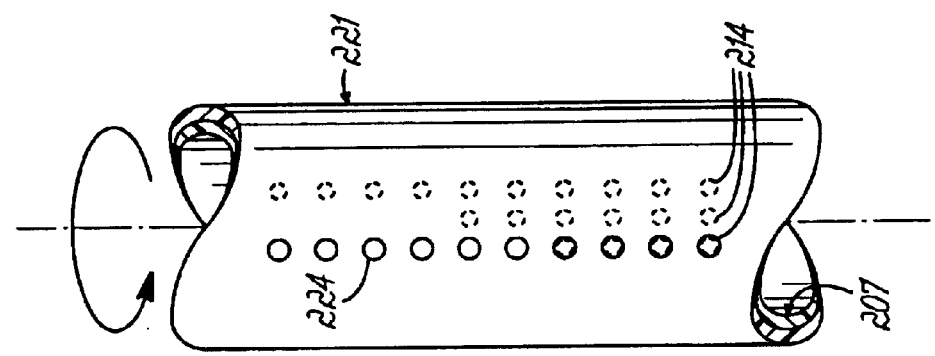
Figure 12A:
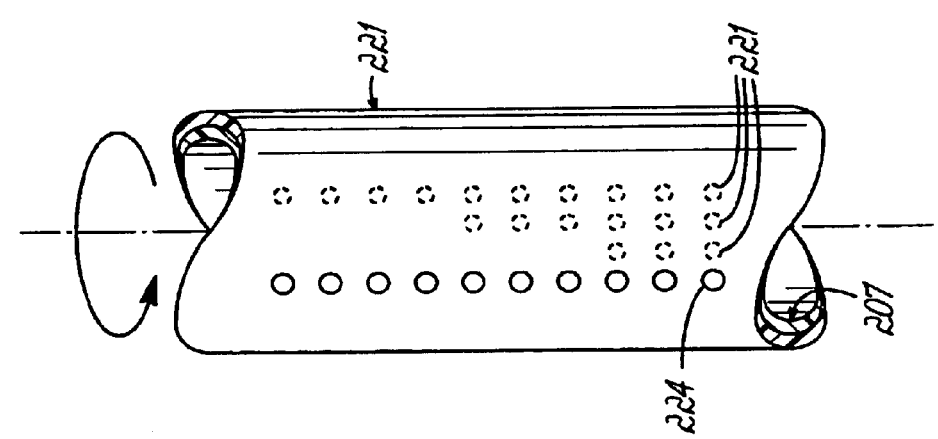
Figures 20, 21:
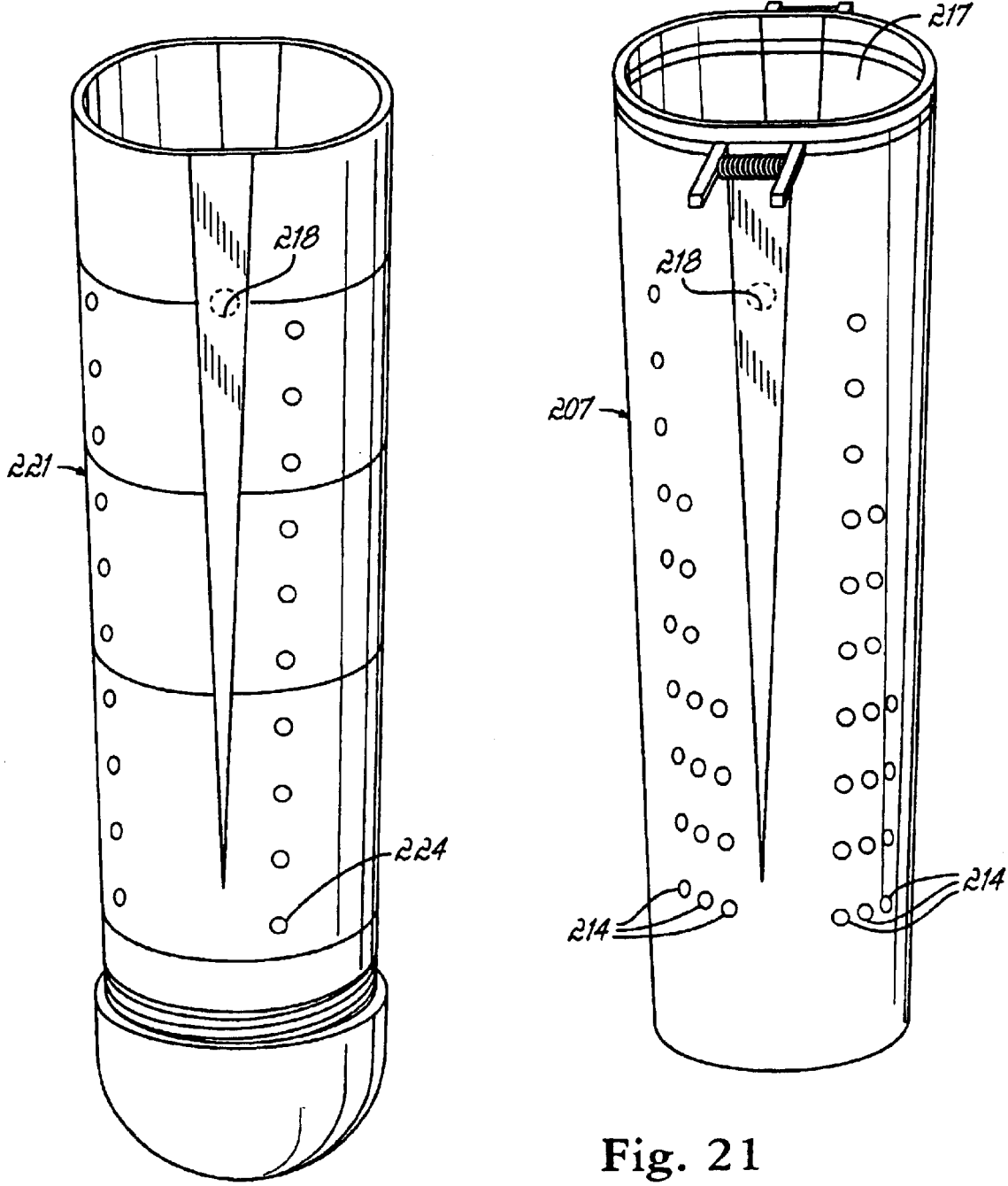
FIG. 20 is a side view of the outside sleeve of an alternative embodiment of the present invention.
FIG. 21 is a side view of the inside sleeve of an alternative embodiment of the present invention.
Figure 22:
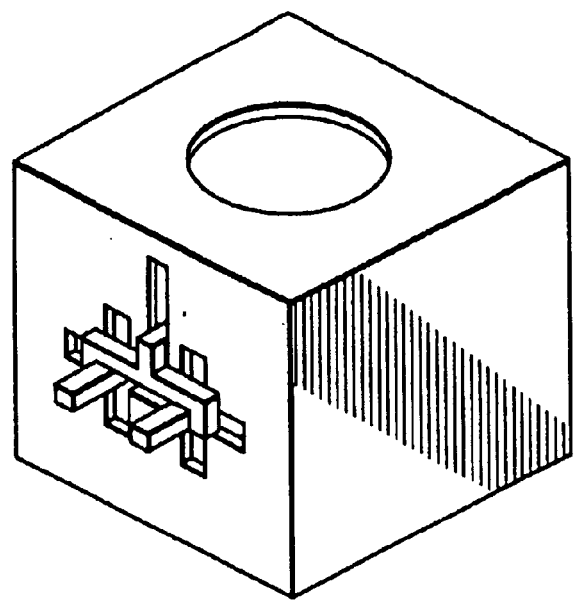
FIG. 22 is a perspective view of locking mechanism of an alternative embodiment of the present invention for reducing the volume of the void between outside sleeve and inside sleeve.
Figure 23:
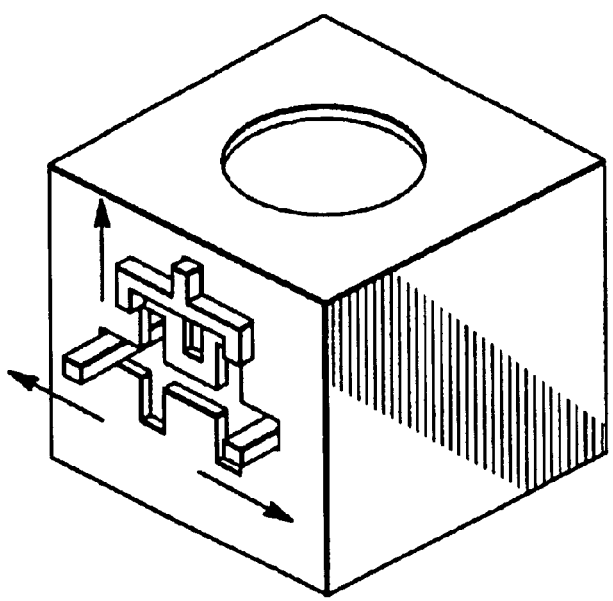
FIG. 23 is a perspective view of a locking mechanism of FIG. 22 of an alternative embodiment of the present invention.
Figure 24:
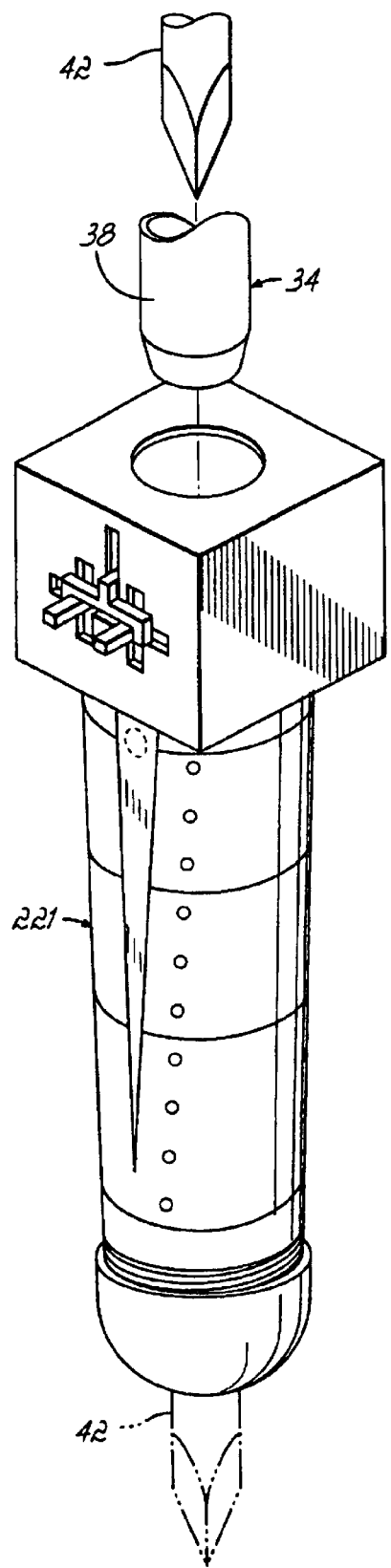
FIG. 24 is a perspective view of an alternative embodiment of the present invention showing orientation of the device with respect to a trocar assembly.
Figure 25:
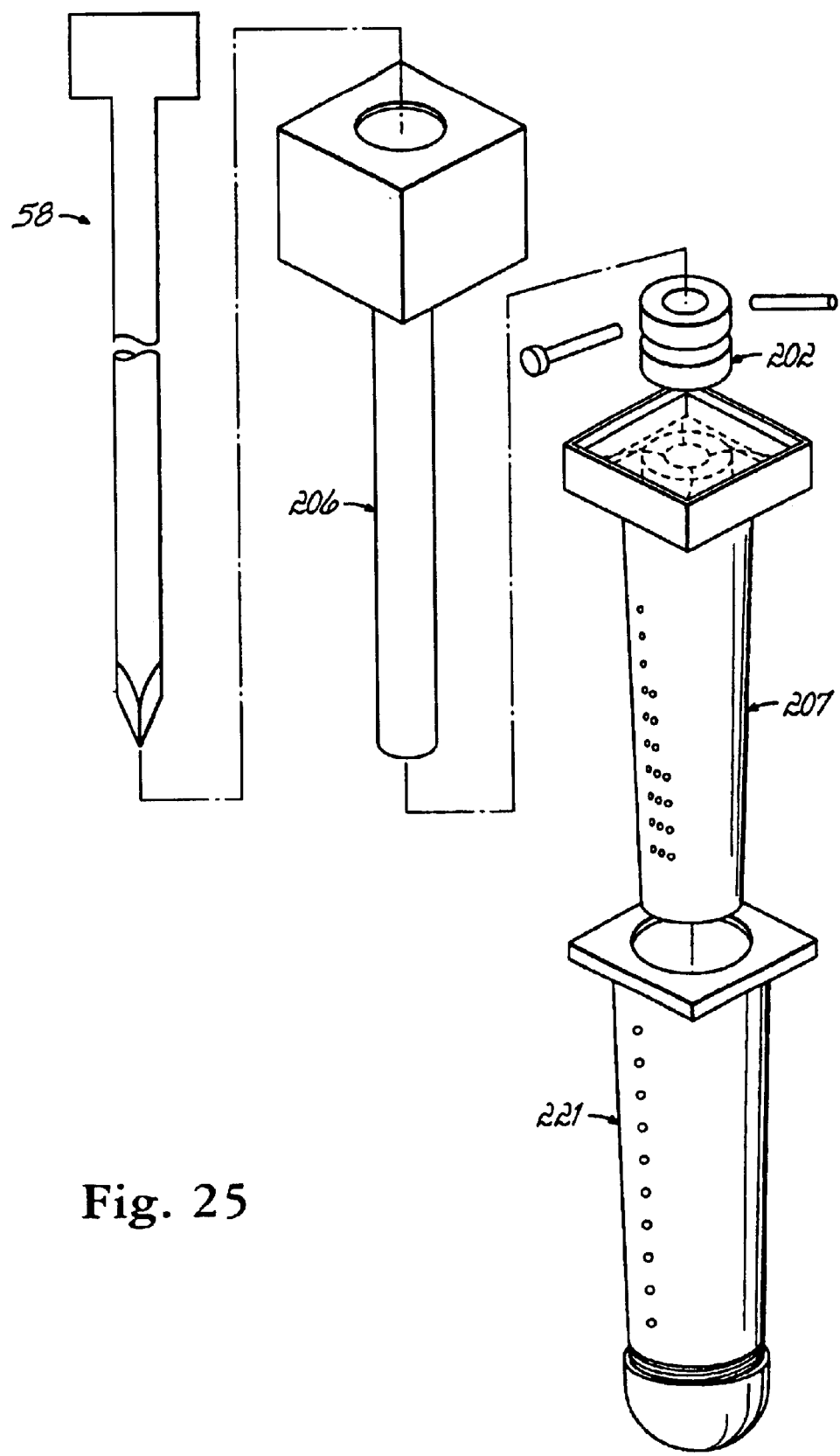
FIG. 25 is an exploded view of the exemplary embodiment of a trocar assembly which incorporates various characteristics of the present invention therein.
Figure 26:
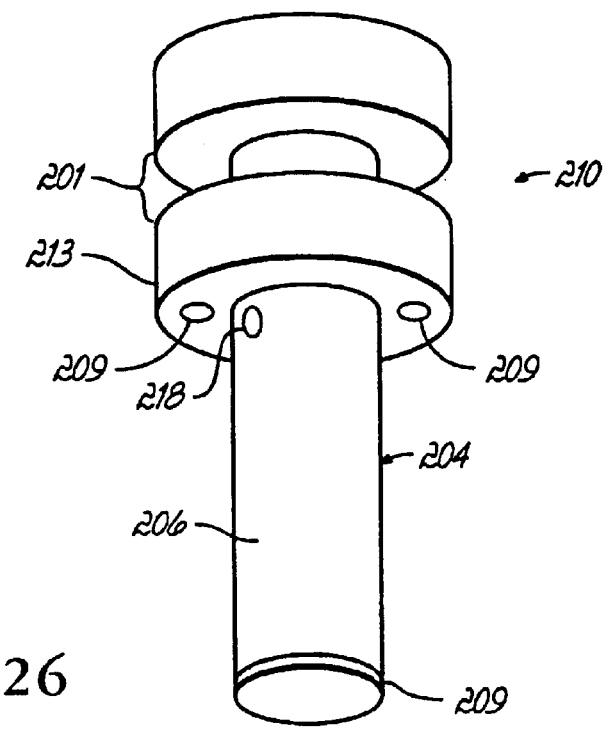
FIG. 26 is side view of a cannula housing.
Figure 27:
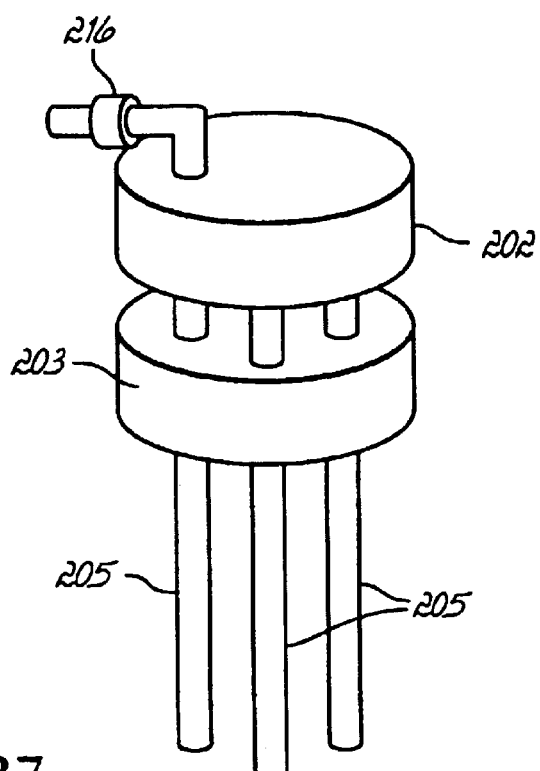
FIG. 27 is a side view of an inflatable bladder.

For example, as shown in FIG. 4, one exit port, i.e. exit port 18, of the plurality of exit ports 30 is shown in the closed mode of operation, that is helical portion 48 is positioned over exit port 18 so as to prevent fluid from being advanced therethrough. In addition, exit ports 20 and 132 are also positioned in a closed mode of operation. In particular, helical portion 50 is positioned over exit port 20 and helical portion 66 is positioned over exit port 132. However, as shown in FIG. 5, moving actuating rods 86 and 92 in the direction indicated by arrow 134 moves helical portion 48 away from exit port 18, thereby placing exit port 18 in the open mode of operation so as to allow fluid to be advanced therethrough. In particular, as shown in FIG. 10 helical portions 48 and 50 are initially located within helical groove 72, with guides 74 positioned within helical groove 106. Upon moving actuating rod 86 in the direction indicated by arrow 134, helical portion 48 is also moved in the direction indicated by arrow 134 since actuating rod 86 is secured to helical portion 48. Moving helical portion 48 as described above causes, helical portion 48 to move out of helical groove 72 as shown in FIG. 11 thereby placing exit port 18 in the open mode of operation such that fluid can advance through exit port 18 in the direction indicated by arrow 140. It should be understood that the movement of actuating rod 86 in the above described manner does not cause helical portion 50 or 66 to move relative to conduit 12 because actuating rod 86 is not secured to these helical portions, and thus exit ports 20 and 132 remain in the closed mode of operation.

It should also be understood that if desired, one of, or both, exit ports 20 and 132 can be placed in the open mode of operation along with exit port 18. In particular, as shown in FIG. 6, if it is desired that exit port 20 also be placed in the open mode of operation, and exit port 132 be left in the closed mode of operation, then actuating rods 88 and 94 (not shown in FIGS. 4–6; see FIG. 2) are moved relative to conduit 12 in the direction indicated by arrow 134 so as to move helical portion 50 away from exit port 20, and thus place exit port 20 in the open mode of operation. Thus it should be understood that the exit ports associated with each helical portion 48, 50, and 66 can be selectively placed in an open mode of operation or a closed mode of operation depending upon the movement of the appropriate actuating rods.

Now referring to FIG. 3, base plate 70 is secured to locking ring 84 so that hole 128 defined in base plate 70 is aligned with lumen 14 of conduit 12. Trocar assembly 58 is advanced through hole 128 of base plate 70 and positioned within lumen 14 of conduit 12 such that a space 36 is defined between an interior surface 40 of conduit 12 and an exterior surface 38 of cannula 34. It should be appreciated that positioning trocar assembly 58 in the above described manner brings exterior surface 38 of cannula 34 into contact with (i) bearing member 126 which is attached to interior surface 116 of locking ring 84 (see FIG. 2) and (ii) bearing member 76 (see FIG. 1) which is attached to interior surface 40 of conduit 12. By placing cannula 34 into lumen 14 of conduit 12 such that exterior surface 38 of cannula 34 is (i) in contact with bearing members 126 and 76 and (ii) spaced apart from interior surface 40, a reservoir 22 is formed as shown in FIG. 3. In particular, reservoir 22 is defined by exterior surface 38 of cannula 34, interior surface 40 of conduit 12, bearing member 76, a portion of interior surface 166 of locking ring 84, and bearing member 126. It should be appreciated that injection port 122 leads to space 36 so that any fluid injected into injection port 122 is disposed in reservoir 22. In addition, it should be appreciated that reservoir 22 is sealed such that any liquid injected into injection port 122 remains in reservoir 22 unless, as discussed in more detail below, dispensing mechanism 28 is manipulated in such a way as to place one or more of the exit ports defined in conduit 12 in the open mode of operation.

During use of body cavity access assembly 10, obturator 42 is initially positioned within passageway 44 of cannula 34 and trocar assembly 58 is located with lumen 14 of conduit 12 as described above (see FIG. 1). In addition, a fluid or liquid preferably containing a biologically active compound 26 (see FIG. 3) is disposed in reservoir 22. In particular, a syringe (not shown) is filled with a predetermined volume of a liquid 26 containing an appropriate amount of biologically active compound, as necessary for the procedure, and the hypodermic needle of the syringe is inserted through diaphragm 130 of injection port 122. The predetermined amount of liquid 26 is then advanced from the syringe through the hypodermic needle and into reservoir 22 in a well known manner. It will be appreciated that other manners of containing liquid 26 prior to dispensing thereof may be used as well. Once an appropriate amount of liquid 26 has been disposed within reservoir 22 the hypodermic needle of the syringe is withdrawn from diaphragm 130 of injection port 122. It should be understood that diaphragm 130 will self seal once the hypodermic needle is removed therefrom to prevent any liquid 26 from leaking out through injection port 122.

Figure 7:
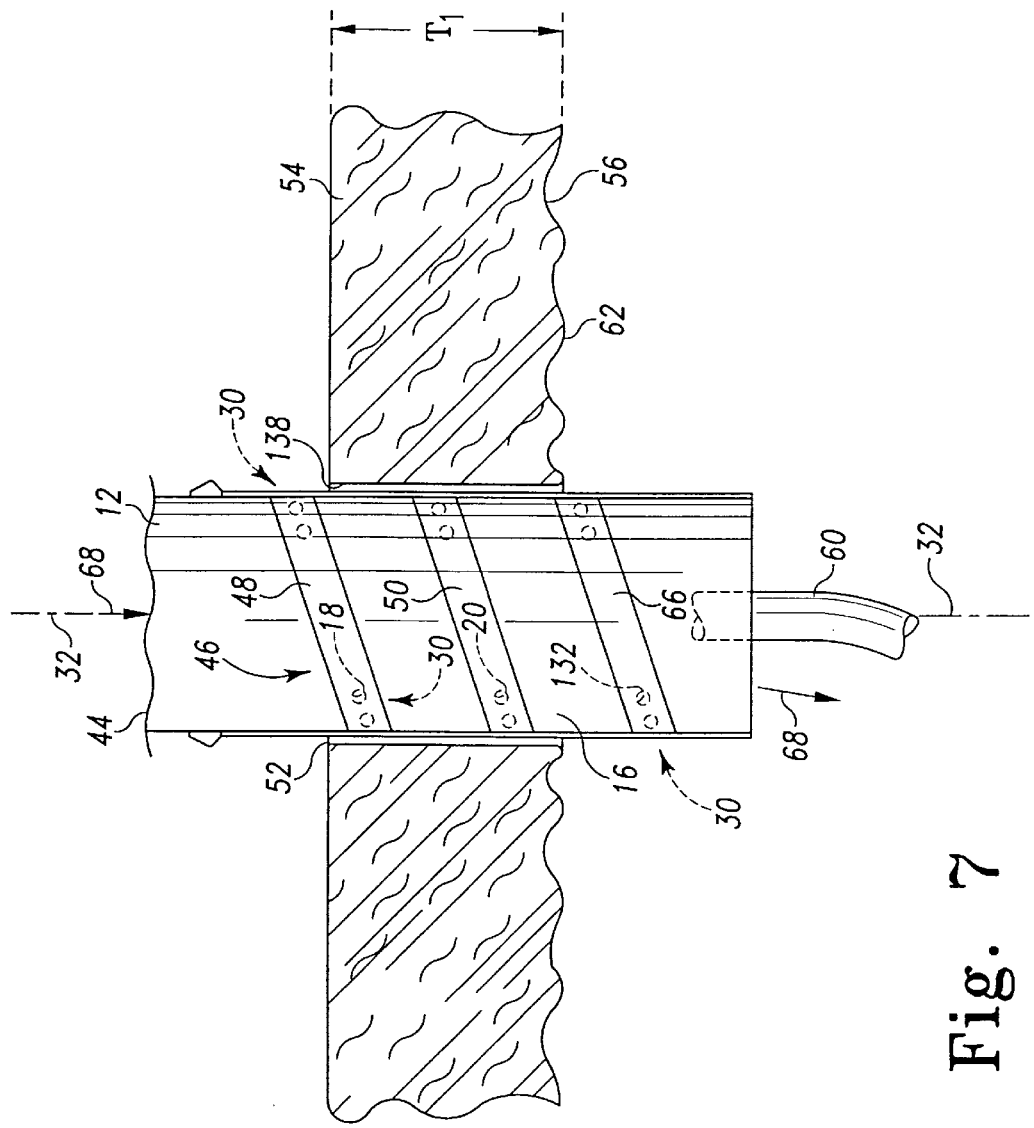

As shown in FIG. 3, once reservoir 22 is loaded in the above described manner, obturator 42 is placed in contact with, and advanced through, a wall 54 of a body cavity 56 to an create opening 52 as shown in FIG. 7. Note that conduit 12 and cannula 34 are also advanced through wall 54 along with obturator 42. Preferably, body cavity access assembly 10 is advanced through a wall 54 of a non-vascular body cavity 56. What is meant herein by non-vascular body cavity 56 is a body cavity which is not defined by one or more blood vessels. Examples of non-vascular body cavities 56 in which body cavity access assembly 10 is preferably used include the peritoneal cavity and the thoracic cavity. Once body cavity access assembly 10 is positioned as described above, obturator 42 is completely removed from passageway 44 of cannula 34. An insufflation gas, such as pressurized $CO_2$, is then advanced from a gas source 142 into passageway 44 of cannula 34 in the direction of arrow 68 as shown in FIG. 7. Once in passageway 44 the insufflation gas is advanced into body cavity 56 to cause insufflation thereof. Once body cavity 56 is insufflated a medical instrument, such as a laparoscope 60, is inserted down through passageway 44 and lumen 14 and into body cavity 56 such that a surgeon can visually inspect the interior of body cavity 56 for possible signs of cancer (e.g. the presence of a tumor in body cavity 56) or an infection. Therefore, it should be appreciated that the cross-sectional area of passageway 44 and lumen 14 should be sized for the passage of a laparoscope therethrough. For example, typical laparoscopes have diameters of about 5 mm to about 10 mm. Thus, passageway 44 and lumen 14 should have a diameter or cross-sectional area sized to accommodate the insertion of a laparoscope therethrough. After inspecting the interior of body cavity 56 with a laparoscope and no signs of cancer or infection are detected, and the surgeon is satisfied that no cancer or infection is present within body cavity 56, the plurality of exit ports can be left in the closed mode of operation and the surgical procedure can proceed in a manner that is well known in the art.

However, if cancer or infection is detected within body cavity 56, or if the surgeon suspects cancer or an infection is present, the surgeon can selectively place an appropriate number of exit ports in the open mode of operation as discussed above. For example, as shown in FIG. 7 if body cavity wall 54 has a thickness $T_1$ such that when conduit 12 is positioned within opening 52 exit ports 18 and 20 are located within opening 52 and exit port 132 is located within body cavity 56, the surgeon may want to only move actuating rods 86, 92, 88, and 94 so as to place exit ports 18 and 20 in the open mode of operation, while leaving exit port 132 in the closed mode of operation. Note that any other exit ports located under helical portions 48 and 50 will also placed in the open mode of operation upon moving actuating rods 86, 92, 88, and 94 in the above described manner. Placing exit ports 18 and 20 in the open mode of operation allows the liquid 26 disposed within reservoir 22 to be advanced through exit ports 18 and 20 and be disposed on exterior surface 16 of conduit 12. Once liquid 26 is disposed on exterior surface 16, it is transferred to side wall 138 of opening 52. Once located in contact with side wall 138, the biologically active compound in liquid 26 may establish a "pharmacological barrier" that helps prevent tumor cell implantation in opening 52 and/or the contamination of opening 52 with viable infectious microbes. Therefore, once opening 52 is protected in the above described manner the surgical procedure can proceed.

Figure 8:
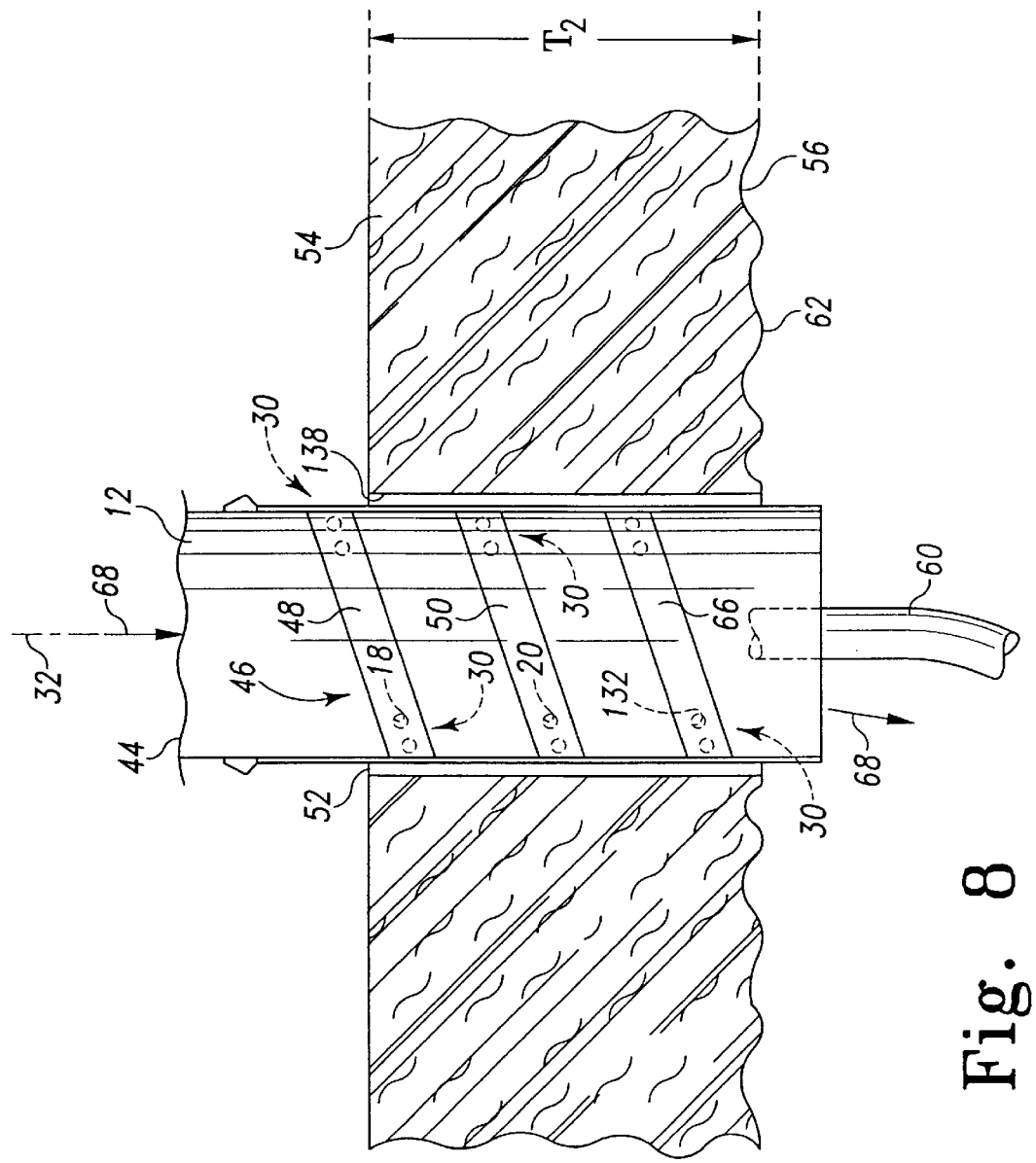

However, if as shown in FIG. 8 the body cavity wall 54 has a greater thickness $T_2$ such that when conduit 12 is positioned within opening 52 exit ports 18, 20, and 132 are located within opening 52, the surgeon may want to move actuating rods 86, 92, 88, 94, 90, and 96 (i.e. all of the actuating rods) so as to place the entire plurality of exit ports 30, including exit ports 18, 20, and 132, in the open mode of operation, and thus ensuring that the entire side wall 138 of the thicker body cavity wall 54 comes into contact with liquid 26. Thus, it should be appreciated that body cavity access assembly 10 provides a surgeon with the flexibility to selectively determine where along the longitudinal axis 32 of conduit 12 the liquid 26 is to be released. Being able to selectively determine where liquid 26 is to be released allows a surgeon to properly protect the side walls 138 of relatively thick and relatively thin body cavity walls 54 from tumor cell implantation or infection with biologically active compound(s) in liquid 26.

The biologically active compound can include chemicals such as antibiotics, cytotoxic agents or compounds which effectively inhibit tumor cell adherence to a membrane. A large number of antimicrobial agents (i.e. antibiotics) or antiseptics are contemplated for use as biologically active compound 26 in the present invention. Preferably, where possible, the antibiotic should be active against both Gram-positive and Gram negative pathogens. The following are illustrative of the antibiotics and/or antiseptics which can be disposed in reservoir 22 or otherwise used in accordance with the invention to aid in the control, inhibition, or prevention of infections of opening 52: (i) metal salts, or like compounds with antibacterial metal ions, e.g. copper or silver, and optionally with additional nonmetallic ions of antibacterial properties; (ii) topical antibiotics, e.g. neomycin, soframycin, bacitracin, polymcin; (iii) antibacterials such as chlorhexidine and its salts; (iv) quaternary ammonium compounds, e.g. centrimide, domiphen bromide, and polymeric quaternaries; (v) iodophors such as povidone iodine, and polyvinylpyrrolidone-iodine (PVP-1); (vi) acridine compounds such as 9-aminoacridine, 3,6-diaminoacridine and 6,9-diamino-2-ethoxyacridine; and (vii) biguanidine compounds such as 1,6-di(4-chlorophenylbiguanido)hexane, diaminohexylbiguanide, 1,6-di(aminohexylbiguanido)hexane, and polyhexamethylenebiguanide. Additional suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Antibiotics such as polymyxin B sulfateneomycin sulfate, cleocin phosphate® (available from the Upjohn Company, Kalamazoo, Mich.) and erythromycin ethylsuccinate are also contemplated.

Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride and silver salts such as silver sulfadiazine, mafenide, nitrofurazole, cloflucarban, tribromasalan, taurolin and noxythiolin.

With respect to aiding in the control, inhibition or prevention of tumor cell adhesion and implantation and the subsequent metastasis via opening 52, compounds which effectively block or inhibit tumor cell adhesion (please note that tumor cell adhesion is a step in the metastasis cascade), or destroy tumor cells before adhering to a side wall 138 of opening 52, or other sites, can be disposed in reservoir 22. Types of compounds which effectively block or inhibit tumor cell adherence include anticoagulants, fibrinolytic agents and compounds which alter the electrical charge of a membrane surface. For example, the surface charge altering and anticoagulant heparin can be disposed in reservoir 22. Additionally, any of several water-soluble high molecular weight glucose polymers (average molecular weight (MW) 75 kdal) otherwise known as dextrans, can also be disposed in reservoir 22 to alter the surface electrical charge of any contacted membranes thereby blocking tumor cell adhesion. Preferably a dextran having an average MW of about 40 kdal is utilized.

As stated above, tumor cell destroying compounds, hereinafter referred to as cytotoxic compounds, can also be disposed in reservoir 22. These compounds include cisplatin, carboplatin, 5-fluorouracil, providoneiodine, tumor necrosis factor (TNF)-a, tauromustine, mitomycin C, camptothecin, bleomycin, indomethacin, -methyl formamide, tamoxifen, sodiumhypochlorite, chlorhexidinecetrimide, adriamycin, methotrexate. Tumor cell destroying compounds also include antimetabolites such as cytarabine, azaribine, mercaptopurine, thioguanine; natural products such as vinblastine, vincristine, dactinomycin, daunorubicin, doxorubicin, bleomycin, mithramycin, mitomycin; and other miscellaneous agents such as cisplatin, hydroxyurea, procarbazine and mitotane, Alkylating agents such as mechlorethamine, nitrogen mustards, ethlenimine derivatives, alkyl sulfonates, nitrosoureas, and triazenes are also contemplated. Moreover, the compounds disclosed by Krakoff, Irwin H. in *Systemic Treatment of Cancer*, CA Cancer J. Clin., vol. 46, No. 3, pages 134–141 (May/June 1996), which is incorporated herein by reference, are contemplated for being used in accordance with the invention.

In addition antiangiogenesis agents such as angiostatin and endostatin are included in the group of cytotoxic compounds to be used as the biologically active compound. Moreover, antibodies, including human monoclonal antibodies are included as cytotoxic compounds. Preferably, the human monoclonal antibody HuMab SK1 as described by Chang, Helena R. et al. in *Human Monoclonal Antibody SK1-Mediated Cytotoxicity Against Colon Cancer Cells*, Dis. Colon Rectum, vol. 36, No. 12, pages 1152–1157 (December 1993) which is incorporated herein by reference, is disposed in reservoir 22. Other monoclonal antibodies can also be used, for example those produced from hybridomas having the accession numbers HB8573, HB8232 and HB8250 available from the American Type Culture Collection, located at 12301 Parklawn Drive, Rockville Md., 20852. Furthermore, interleukin 2 (IL-2), cytokines or lymphokines are also included in the group of cytotoxic compounds of the present invention. Also contemplated are hyaluronate coating solutions. In addition, gene based cancer drugs are contemplated. Examples of such include gene based cancer drugs directed toward the RAS gene. Another example of a gene based cancer drug is a drug directed toward the EGF receptor (i.e. EGFR). It should also be understood that a combination of any of the above compounds can be disposed in reservoir 22.

If necessary, in order to keep liquid 26 from falling or sliding off exterior surface 16 of conduit 12 due to gravity, or being advanced out of exit ports 30 to quickly, liquid 26 can contain a suitable pharmaceutically acceptable carrier. Such pharmaceutically acceptable carriers include known excipients and auxiliaries which facilitate the processing of liquid 26 into a preparation such as a fluid which has the appropriate consistency to be advanced out of exit ports 30 in a controlled manner and thus disposed on exterior surface 16 of conduit 12 and side wall 138 of opening 52.

Suitable excipients which may be used to prepare a pharmaceutically acceptable carrier, such as a paste or a viscous solution, include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or alginic acid or a salt thereof, such as sodium alginate. Additionally, silica, talc, stearic acid or salts thereof such as magnesium stearate or calcium stearate, and/or polyethylene glycol can be used.

In addition, a suspension of biologically active compound may be disposed on outer surface 16 or side wall 138. Suitable vehicles for such suspensions include sesame oil or synthetic fatty acid esters, for example, ethyl oleate or triglycerides. Such suspensions can include substances which increase the viscosity of the suspension including, for example, sodium carboxymethyl cellulose, sorbitol and/or a dextran.

The exact formulation of a pharmaceutically acceptable carrier will depend upon the particular nature of biologically active compound to be disposed upon outer surface 16 and is easily determinable by one of ordinary skill in the art from only routine experimentation. The proper dosage regimen of biologically active compound for a particular patient undergoing the above described surgery is dependent upon several factors including the age, sex, weight, condition of the recipient, kind of concurrent treatment, if any, frequency of treatment and the nature of the effect desired. In addition, the dosage regimen will also depend upon the immunologic status of the patient and the aggressiveness of the tumor. Moreover, the amount of biologically active compound administered to the patient should be large enough to produce the desired effect but not so large as to cause adverse side effects, such as unwanted cross reactions, impaired wound healing, bleeding, impaired platelet function, anaphylactic reactions and the like. Counterindication, if any, immune tolerance and other variables will also affect the proper amount administered to the patient. The exact formulation of a pharmaceutically acceptable carrier and the amount of biologically active compound contained therein (and therefore the amount administered to the patient) is easily determinable by one of ordinary skill in the art from only routine experimentation and by applying well know principles of therapeutics as set forth, for example, in Gilman, Alfred G. et al., eds., *The Pharmacological Basis of Therapeutics*, 6$^{th}$ Edition, Macmillan Publishing Co., Inc. New York, N.Y. (1980) which is herein incorporated by reference. Preferably, such preparations will contain about 0.001 to about 99 percent biologically active compound together with the pharmaceutically acceptable carrier.

Body cavity access assembly 10 also allows a surgeon to avoid utilizing a liquid 26 containing a biologically active compound until it is deemed necessary. This is not possible with other methods of delivering a biologically active compound. For example, the dipping of a medical apparatus (e.g. a cannula) in a solution or suspension of biologically active compound must be performed prior to the beginning of the surgery at a time when the surgeon has not visually confirmed the presence of cancer or infection in body cavity 56. The surgeon must dispose biologically active compound on the medical device before the beginning of the surgery since withdrawing the medical apparatus after the surgery has started would cause a loss of the insufflation of body cavity 56 which can complicate the surgical procedure. Therefore, in many circumstances the surgeon will unnecessarily utilize biologically active compound when no cancer or an infection is present which increases the cost of the surgical procedure. This is in contrast to the present invention which allows the surgeon to (1) begin the surgical procedure, (2) confirm whether any biologically active compound is required, and (3) only if needed, administer an accurate controllable amount of biological compound to the patient without interrupting the surgical procedure and withdrawing body cavity access assembly 10 from body cavity 56.

THE EMBODIMENT OF FIGS. 12–30

A housing accommodates a storage reservoir 242, a pump 240, an injection port 218, and an exhaust valve 216. The storage reservoir 242 is filled with chemical through the injection port 218. A pump 240 supplies air through a check valve to the storage reservoir 242 to pressurize the chemical in the storage reservoir 242. At a predetermined pressure in storage reservoir 242, feed valve 241 opens to allow the chemical to transfer to the reservoir 217 and pressurizes reservoir 217. During the chemical transfer from the storage reservoir 242 to the reservoir 217, the pressure in storage reservoir 242 decreases and when the pressure is below a predetermined value, the feed valve 242 closes. A venting valve 216 allows venting the air in the storage reservoir 241 and may be used to facilitate the closing of the feed valve 241.

The chemical in reservoir 217 may be pressurized in an alternative method. A dumbbell shaped housing accommodates the insufflation bladder 202 into space 201. Distension bladder 203 wraps around lower housing section 204. Cannula bladders 205 wrap around cannula sleeve 206. Inside sleeve 207 goes around cannula sleeve 206 with security bows 208 going through security bow latch 209 then insert into nook inside lower portion of the upper housing 210. Security bow 208 allows the inner sleeve 207 to radially dilate but not to rotate. Upper portion 211 of inside sleeve 207 is intimately adjacent to the distension bladder 203. The bowed bias of security bow 208 allows the bladder to dilate the upper portion 211 of inside sleeve 207 when the bladder is dilated.

To proximally seal the reservoir, an O-ring 212 is attached to the undersurface of housing 213 and is lubricated to seal and allow movement of the adjacent structures.

The distribution pattern of the chemical to the port site opening is controlled through the alignment of holes in the inner sleeve 214 with the holes in the outer sleeve 224. Diffusion holes starting distally on the left and going to the middle then up to the proximal area of inside sleeve 207 are noted to enable the chemical in the reservoir 217 to diffuse through the inner sleeve 207. These holes are arranged circumferentially around the inside sleeve 207.

Outside sleeve 221 is friction fit onto inside sleeve 207 and securely mounted onto base extension 222. The lower housing 222 is slidably mounted in a radial direction onto the lower housing 218. This housing 222 may be rotated relative to the fixed inner sleeve 207. Outside sleeve 221 has a single row of vertically mounted and perfectly aligned holes relative to inside sleeve 207 and its holes 214.

The hole alignment selected is determined based on the size of an individual. A thin person has a thinner abdominal wall and therefore requires chemical along only a small portion of the cannula. To provide chemical only along a small portion of the cannula, the surgeon will select the distribution setting where chemical is excreted through a few holes. A heavier person would have a thicker abdominal wall. To coat the entire width of the port site opening of the heavier person would require the excreting of chemical along a longer portion of the cannula. This is accomplished by aligning a longer row of holes of the inside sleeve 214 with the row of holes on the outside sleeve 224.

When outside sleeve 221 is rotated in a counterclockwise direction relative to holes 214, the single row of holes 224 on outside sleeve 221 will be aligned with variously staged holes 214 of the inner sleeve 207. With the first click the holes on cannula 221 are aligned with the distal holes 214. With the next click, the distal and middle holes are aligned and enable the preferential chemical to flow through these holes. When the third click is encountered both visually, indicated by a mark mounted on the housing 225 and felt via a "click" the surgeon knows the entire cannula is coated with a chemical which is flowing along the outer portion of cannula 221 which is adjacent of the patients port site. The lower O-ring 226 is placed under the base plate 222 to seal the device, and it is snapably mounted and secured with the base plate 222 to seal the entire device.

One advantage of this device is it allows the surgeon to place a chemical into the port site while the device is in use. During surgery, the trocar is inserted into the body, when cancer is detected and the surgeon desires to coat the port side opening with biologically active compound, the storage reservoir is filled with the chemical or the storage reservoir is prefilled with the chemical, i.e. biological active substance, the outside sleeve is rotated to align the outside sleeve holes 224 with the inside sleeve holes 214. The surgeon then uses the pump 240 to pressurize the storage reservoir 242 and transfer the chemical to the reservoir 207 and through the inside sleeve holes 214 and outside sleeve holes 224 to the port side opening.

The volume of the storage reservoir 242 can be based on the volume of the reservoir 217 and the desired dose of biological active compound to the patient. To refill the chemical trocar, the storage reservoir 242 is filled with chemical through the injection port 218. The outer sleeve 221 should remain rotated relative to inner sleeve 207 to align the inner sleeve holes 214 with the outer sleeve holes 224 for supplying the desired depth of flow along the axis of the outer sleeve 221 The storage reservoir is then pressurized with air through manual hand pump 240. The chemical moves from the storage reservoir 242 to the reservoir 217 through the inside sleeve holes 214, through the outside sleeve holes 224 to the port site opening.

While the present invention has been illustrated by a description of a preferred embodiment and while this embodiment has been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims, wherein

I claim:

1. A body cavity access assembly, comprising:

a conduit having a lumen through which a medical instrument may be advanced, an exterior surface, a liquid input adapted to be coupled to a source of liquid, said liquid input communicating with a plurality of exit ports defined along a portion of said exterior surface, and a dispensing mechanism operatively coupled to said conduit, said dispensing mechanism being adjustable to selectively open said exit ports thereby allowing the liquid to flow therefrom and to selectively close at least one of said exit ports to prevent the liquid from flowing therefrom.

2. The assembly of claim 1, wherein:

said conduit has a length, and said plurality of exit ports are positioned on said exterior surface of said conduit so that said exit ports are spaced along said length.

3. The assembly of claim 1, further comprising:

a reservoir having an interior void for receiving the liquid, said interior void of said reservoir being in fluid communication with said plurality of exit ports.

4. The assembly of claim 3, further comprising:

a cannula positioned within said lumen of said conduit such that a space is defined between an exterior surface of said cannula and an interior surface of said conduit, wherein said reservoir is positioned within said space.

5. The assembly of claim 4, further comprising:

an obturator positioned within a passageway defined through said cannula.

6. The assembly of claim 1, wherein:

said conduit has an inner diameter $D_1$, and $D_1$ is at least 5 millimeters.

7. The assembly of claim 1, wherein:

said dispensing mechanism includes a helical member disposed around said exterior surface of said conduit, said helical member being rotatable to selectively open and close said plurality of exit ports.

8. A body cavity access assembly, comprising:

a conduit having (i) a lumen through which a medical instrument may be advanced, (ii) an exterior surface, (iii) a first exit port defined in said exterior surface, said first exit port being (A) operable between an open mode of operation and a closed mode of operation and (B) adapted to be in fluid communication with an interior void of a reservoir containing a liquid and (iv) a second exit port defined in said exterior surface, said second exit port being (A) operable between an open mode of operation and a closed mode of operation and (B) adapted to be in fluid communication with said interior void of said reservoir; and a dispensing mechanism operatively coupled to said first exit port and said second exit port, such that (i) said dispensing mechanism can selectively place said first exit port in (A) said open mode of operation so that said liquid may be advanced through said first exit port or (B) said closed mode of operation so that said liquid is prevented from being advanced through said first exit port and (ii) said dispensing mechanism can selectively place said second exit port in (A) said open mode of operation so that said liquid may be advanced through said second exit port or (B) said closed mode of operation so that said liquid is prevented from being advanced through said first second exit port.

9. The assembly of claim 8, wherein:

said conduit has a length, and said first and second exit ports are positioned on said exterior surface of said conduit so that said exit ports are spaced along said length.

10. The assembly of claim 8, further comprising said reservoir with said interior void coupled in fluid communication with said first and second exit ports.

11. The assembly of claim 10, further comprising:

a cannula positioned within said lumen of said conduit such that a space is defined between an exterior surface of said cannula and an interior surface of said conduit, wherein said reservoir is positioned within said space.

12. The assembly of claim 11, further comprising:

an obturator positioned within a passageway defined through said cannula.

13. The assembly of claim 8, wherein:

said conduit has an inner diameter $D_1$, and $D_1$ is at least 5 millimeters.

14. The assembly of claim 8, wherein:

said dispensing mechanism includes a helical member disposed around said exterior surface of said conduit, said helical member being rotatable to selectively place the dispensing mechanism into said open and closed modes of operation.

15. A method for dispensing a liquid during a surgical procedure, comprising:

creating an opening in a wall of a body cavity, advancing a conduit through the opening, said conduit having a lumen through which a medical instrument may be advanced, and an exterior surface having a variable size dispensing zone extending along a length thereof, discharging the liquid from the dispensing zone, changing the size of the dispensing zone, and discharging the liquid from the dispensing zone of changed size.

16. The method of claim 15, wherein the variable size dispensing zone is formed by a plurality of exit ports in the exterior surface of the conduit and changing the size of the dispensing zone further comprises closing off at least one of the exit ports.

17. The method of claim 15, wherein the variable size dispensing zone is formed by a plurality of exit ports in the exterior surface of the conduit and changing the size of the dispensing zone further comprises opening at least one of the exit ports.

* * * * *